United States Patent [19]
Altenbach et al.

[11] Patent Number: 6,018,050
[45] Date of Patent: Jan. 25, 2000

[54] METHOD OF PREPARING OPTICALLY ACTIVE α-AMINO ACIDS AND α-AMINO ACID DERIVATIVES

[75] Inventors: Hans-Josef Altenbach; Matthias Kottenhahn, both of Wuppertal; Annegret Vogt, Allemagne; Mike Matthaus; Andreas Grundler, both of Wuppertal; Michael Hahn, Cologne, all of Germany

[73] Assignee: Degussa Aktiengesellschaft, Frankfurt, Germany

[21] Appl. No.: 09/043,038

[22] PCT Filed: Sep. 11, 1996

[86] PCT No.: PCT/EP96/03984

§ 371 Date: Apr. 30, 1998

§ 102(e) Date: Apr. 30, 1998

[87] PCT Pub. No.: WO97/10203

PCT Pub. Date: Mar. 20, 1997

[30] Foreign Application Priority Data

Sep. 11, 1995 [DE] Germany .............. 195 33 617

[51] Int. Cl.$^7$ ............. C07D 261/20; C07C 239/00; C07C 229/08
[52] U.S. Cl. ............. 548/242; 548/301.7; 560/312; 562/444; 562/449; 562/553; 562/567; 562/574
[58] Field of Search ............. 548/301.7, 242; 562/553, 567, 574, 444, 449; 560/312

[56] References Cited

PUBLICATIONS

Tetrahedron, vol. 44, No. 17 (1988), p5277–92, Fitzi et al, 'Resolution and use in alpha amino acid synthesis of imidazolidinone glycine derivatives'.

*Primary Examiner*—Gary Geist
*Assistant Examiner*—Brian J. Davis
*Attorney, Agent, or Firm*—Omri M. Behr, Esq.

[57] ABSTRACT

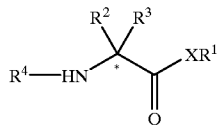

The invention relates to a new process for the preparation of optically active amino acids and amino acid derivatives of the general formula (I), wherein *, X and $R^1$ to $R^4$ have the meaning given in the description. Starting from commercially obtainable (−)-menthol or (+)-menthol, the enantiomerically pure compounds of the formula (I) are obtained in high yields. The method is particularly suitable for the preparation of sterically demanding amino acids and amino acid derivatives.

28 Claims, No Drawings

METHOD OF PREPARING OPTICALLY ACTIVE α-AMINO ACIDS AND α-AMINO ACID DERIVATIVES

RELATED APPLICATIONS

This application is a 371 of PCT/EP96/03984, filed Sep. 11, 1996.

FIELD OF THE INVENTION

The invention relates to a new process for the preparation of optically active amino acid and amino acid derivatives of the general formula I

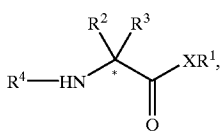

I wherein
  *=centre of asymmetry
  X=O or NH
  $R^1$=H, ($C_1$–$C_6$) alkyl, benzyl or $C_1$–$C_4$) alkoxycarbonyl-methyl and
  $R^2$, $R^3$, independently of one another, denotes H, ($C_1$–$C_6$) alkyl, which can be interrupted or substituted by heteroatoms, such as N. P, O, S or Si, it being possible for the heteroatoms themselves to be substituted by ($C_{1-3}$) alkyl once or several times, ($C_{2-6}$) alkenyl, ($C_1$–$C_6$) haloalkyl, halogen, aryl, such as naphthyl or phenyl, which can be substituted by ($C_1$–$C_3$) alkyl, hydroxyl, halogen or ($C_{1-3}$) alkoxy once or several times, aralkyl, such as 2-naphthylmethyl or benzyl, which in its turn can be substitutes by ($C_1$–$C_3$) alkyl, hydroxyl, halogen or ($C_{1-3}$) alkoxy once or several times, heteroaralkyl, such as N-protected 3-indolylmethyl, and
  $R^4$=H,
wherein if $R^2$=H, $R^3$≠H, Proteinogenic amino acids are known as the building blocks of life. These α-amino acids can be incorporated into peptides or used in amino acid or peptide mixtures, such as infusion solutions. However, non-proteinogenic α-amino acids are also increasingly being incorporated into peptides, not to compensate naturally occurring deficits but to be able to have a targeted action on reaction sequences in the mechanism of the body.

The branched amino acids in particular are also important starting substances in the field of asymmetric synthesis. For the fields of use mentioned, it is decisive that the amino acids mentioned are obtainable in the highest possible chemical and optical purity.

DISCUSSION OF THE PRIOR ART

Tetrahedron 44 (1988) 5277 thus describes a process which uses R- or S-tert.butyl-methyl-imidazolidinone (R- or S-BMI) in protected form as a glycine α-anion equivalent. The process for the preparation of the enantiomerically pure building block mentioned is initially based on the racemic three-stage synthesis. After aminolysis of glycine methyl ester hydrochloride with monomethylamine in methanol, the glycine methylamide formed is subjected to a condensation reaction with pivaldehyde in methyl tert-butyl ether to give the Schiff's base, which is then cyclized in ethanol with an ethanolic HCl solution to give rac-BMI hydrochloride. Finally, the enantiomers are separated with (R)-mandelic acid (EP 0 542 099 A2). The R- or S-BMI thus obtained can then be alkylated and cleaved to give the amino acid.

Aldrichimica Acta 25 (1992) 11 describes another process which is based on a chiral oxazinone and which can function both as a glycine α-anion equivalent (in the form of its BOC-protected derivative) and as a glycine α-cation equivalent (after NBS bromination in $CCl_4$). erythro-1,2-Diphenylethanolamine serves as a chiral auxiliary function, and is obtained by racemate splitting with L-glutamic acid or by asymmetric Sharpless dehydroxylation. The enantiomerically pure amino acids are obtained oxidatively or reductively. The alkylation of the glycine enolate is typically carried out in THF by addition of a strong base to the mixture of the oxazinone and the electrophile at –80 ° C. If the reaction conditions are not carefully adhered to, undesirable dialkylation product is observed, in addition to unreacted starting material. A targeted second alkylation to give a,cac-substituted derivatives can be realized with reactive alkyl halides (allyl, benzyl) exclusively at very low temperatures (e. g. –80 ° C.). The complementary glycine α-cation route makes use of an α-bromo derivative, which is obtained by NBS bromination in $CCl_4$. The unstable substance is used directly as the crude product for the alkylation. In the presence of zinc chloride, a range of organometallic reagents can be employed (organotin, -silicon, -copper, -zinc compounds). The cation route (α-halo derivative) gives alkyl and aryl derivatives in yields of between 39 and 82%, from which α-amino acids are obtainable with an ee of 82% to 99%

The process variants described have the disadvantages that they give only moderate yields, especially with sterically demanding amino acids, in some cases require very many reaction steps, form intermediate products which are unstable and cannot be stored, and destroy the stereo-centre of the chiral auxiliary during the hydrolysis and therefore render recycling of the auxiliary impossible.

The object of the invention is accordingly to provide a process which does not have the disadvantages mentioned and furthermore proceeds economically.

SUMMARY OF THE INVENTION

The object of the invention for the preparation of amino acids and amino acid derivatives of the general formula I

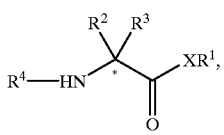

I wherein
  *=centre of asymmetry
  X=O or NH
  $R^1$H =($C_1$–$C_6$) alkyl, benzyl or ($C_1$–$C_4$) alkoxycarbonyl-methyl and
  $R^2$, $R^3$, independently of one another, H, ($C_1$–$C_6$) alkyl, which can be interrupted or substituted by heteroatoms, such as N, P, O, S or Si, it being possible for the heteroatoms themselves to be substituted by ($C_1$–$C_3$) alkyl once or several times, ($C_2$–$C_6$) alkenyl, ($C_1$–$C_6$) haloalkyl, halogen, aryl, such as naphthyl or phenyl, which can be substituted by ($C_1$–$C_3$) alkyl, hydroxyl, halogen or ($C_1$–$C_3$) alkoxy once or several times, aralkyl, such as 2-naphthylmethyl or benzyl, which in its turn can be substituted by $(C_1-C_3)$ alkyl, hydroxyl, halogen or $(C_{1-3})$ alkoxy once or several times, heteroaralkyl, such as N-protected 3-indolylmethyl, and $R^4$=H, wherein if $R^2$=H, $R^3$ X H, is achieved by a procedure in which a general compound of the formula II

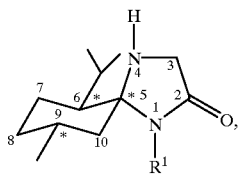

II wherein *, $R^1$ have the abovementioned meaning,
a) is converted by oxidation into a compound of the general formula III

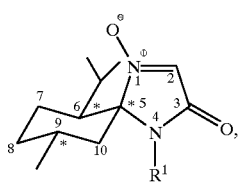

III wherein *, $R^1$ have the abovementioned meaning, and
b) the compounds of the general formula III are reacted with a nucleophile to give compounds of the general formula IV

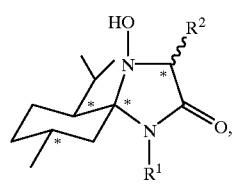

IV wherein *, $R^1$ and $R^2$ have the abovementioned meaning, and
c) the compounds of the general formula IV are reduced to give the compounds of the general formula V

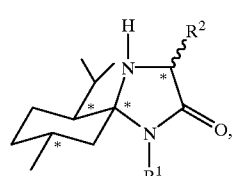

V wherein *, $R^1$ and $R^2$ have the abovementioned meaning, and
d) the compounds of the general formula V are then hydrolysed to give the L-α-amino acids or L-α-amino acid derivatives or D-α-amino acids or D-α-amino acid derivatives of the general formula I or of an acid addition salt thereof, or in which process steps a) and b) are carried out and then
e) the compound of the general formula IV is oxidized to give compounds of the general formula VI

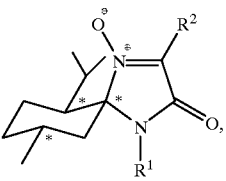

VI wherein *, $R^1$ and $R^2$ have the meaning already given, and VI is converted by reaction with a nucleophile into compounds of the general formula VII

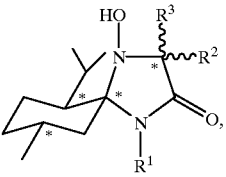

VII wherein *, $R^1$, $R^2$ and $R^3$ have the meaning already given, and
f) compounds of the general formula VII are reduced to give compounds of the general formula VIII

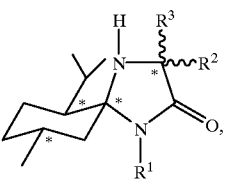

VIII wherein *, $R^1$, $R^2$ and $R^3$ have the abovementioned meaning,
and then
g) these are hydrolysed to give the α,α-dialkylamino acids or α,α-dialkylamino acid derivatives of the general formula I or of an acid addition salt thereof.

DESCRIPTION OF THE PREFERRED EMBODIMENTS

Amino acids and amino acid derivatives of the general formula I or of an acid addition salt thereof

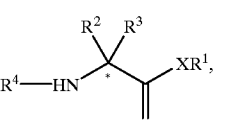

I wherein
$R^1$=$(C_1-C_4)$ alkyl or benzyl,
$R^2$, $R^3$, independently of one another, denote H, $(C_1-C_6)$ alkyl, which can be interrupted or substituted by heteroatoms, such as N, P, O, S or Si, it being possible for the heteroatoms themselves to be substituted by $(C_1-C_3)$ alkyl once or several-ttimes, $(C_1-C_6)$ alkenyl, $(C_1-C_6)$ haloalkyl, aryl, such as phenyl, which can optionally be substituted by halogen once or several times, aralkyl, such as benzyl, which in its turn can be substituted by ($C_1$–$C_3$) alkyl, hydroxyl or ($C_1$–$C_3$) alkoxy once or several times, and $R^4$=H, can particularly preferably be obtained by the process according to the invention, wherein if X=0, $R^1$ can be=H, and if $R^2$=H, $R^3 \neq$H.

The term "alkyl groups" is to be understood as meaning both "straight-chain" and "branched" alkyl groups. The term "straight-chain alkyl group" is to be understood as meaning, for example, radicals such as methyl, ethyl, n-propyl, n-butyl, n-pentyl, n-hexyl, and "branched alkyl group" is to be understood as meaning radicals such as, for example, isopropyl, neopentyl or tert.-butyl. The term halogen represents fluorine, chlorine, bromine or iodine. The term "alkoxy group" represents radicals such as, for example, methoxy, ethoxy, propoxy, butoxy, isopropoxy, isobutoxy or pentoxy.

In the compounds of the structure type IV, V, VII, VIII, IX, X, XI, XII and XIII, the nomenclature corresponds to the structure type II. In the compounds of the type VI, the nomenclature of III is to be assumed.

Compared with the known processes, the new process allows a novel reaction procedure which renders simpler and faster preparation of the compounds of the general type I possible. Depending on the starting material chosen, L-α-amino acids or D-α-amino acids or, in a further reaction step, optically active α,α-dialkylamino acids and derivatives thereof can be synthesized in a targeted manner.

Thus, advantageously, starting from (−)-menthol the corresponding L-α-amino acids or their derivatives can be obtained, and starting from the optical antipode (+)-menthol the corresponding D-α-amino acids and their derivatives can be obtained. Identification of the asymmetric carbons in the cyclohexane fragment of the compounds of the general formulae II to XIII with * is intended to illustrate that this is an optically pure stereo-centre of the configuration 6S,9R or 6R,9S, depending on the starting material (−)-menthol or (+)-menthol chosen. The unambiguous and absolute configuration of the further centres of asymmetry identified with * results from the choice of starting substances. Thus, in II, the centre 5R or 5S is determined unambiguously by 6S,9R or 6R,9S respectively. Identification of a bond in the general formulae with means that this is a centre of asymmetry with an unambiguous and absolute configuration S or R. (−)-Menthol or (+)-menthol is converted here into the corresponding (−)-menthone or (+)-menthone respectively by oxidation in a manner known per se from the literature (Houben-Weyl "Methoden der Organischen Chemie [Methods of Organic Chemistry]", vol. 7/2a, p. 724). The compounds of the general type II are also prepared in a manner known per se (Houben-Weyl, 11/2, p. 73 et seq.; EP 0 542 099 A2), for example by reaction of glycine methyl ester hydrochloride with an alcoholic solution, preferably an ethanolic solution, of an amine (at room temperature and with exclusion of moisture. (+)- or (−)-menthone is then added to the suspension in the presence of a base and the mixture is refluxed. The water of reaction can be removed in the conventional manner, and a molecular sieve (3 Å) is preferably used. When the reaction has ended, the solvent is removed, the residue is taken up in a two-phase system of water/org. solvent, the aqueous phase is extracted several times with an organic solvent and the organic phase is then dried. The purification can be carried out by distillation or recrystallization.

The oxidation reaction to give compounds of the type III (nitrone) can also be carried out in a manner known per se (Houben-Weyl, E 14b, p. 1409 et seq.). For this, for example, II is dissolved in an organic solvent, such as methylene chloride, acetone or methanol, and reacted with an oxidizing agent, such as, for example, m-chloroperbenzoic acid, hydrogen peroxide in the presence of sodium tungstate, selenium dioxide or dimethyldioxirane. When the reaction has ended, the excess oxidizing agent is destroyed, the organic phase is separated off, the aqueous phase is rinsed several times with a suitable solvent and the collected organic phases are dried. Further purification can be carried out by recrystallization from an organic solvent. TV The nitrone III represents a hitherto unknown glycine α-cation equivalent. In contrast to the syntheses known to date, it is a crystalline substance which can be stored and can be reacted highly selectively with a wide range of nucleophiles. After recrystallization or purification by column chromatography, the alkylated diastereomerically pure derivatives IV are present in yields of between 39 and 83%.

The reaction of compounds of the structure type III to give compounds of the general formula IV is carried out with exclusion of moisture and air, e. g. under a nitrogen or argon atmosphere. For this, the compounds of the type III are dissolved in an organic inert solvent, such as DMSO or an ether, for example diethyl ether, diisopropyl ether, dimethoxyethane, THF, dioxane, or an aromatic hydrocarbon, such as toluene, chlorobenzene, xylene, or a halogenated hydrocarbon, such as methylene chloride, or alcohols, such as methanol, ethanol or isopropanol, diethyl ether or toluene being particularly preferred, and the solution is brought to a temperature of between −20° C. to −80° C., preferably −40° C. to −60° C., particularly preferably −50° C., before 1.0 to 5.0 equivalents, preferably 2.0–3.0 equivalents, of a nucleophile (cf. Lit. P. D. Bailey, J. Clayson, A. N. Boa, Contemp. Org. Syn. 2(3) 1995, 173, α-cation equivalents of amino acids), typically of an organometallic compound, such as, for example, an organolithium compound, organocopper compound, organomagnesium compound (Grignard compound), organozinc, -tin, -silicon, -cadmium compounds or deprotonatea CH-acid compounds, such as nitromethane, as well as cyanide, are added. When the reaction has ended, the reaction mixture is worked up in the conventional manner under aqueous conditions, for example with ice-cold, half-saturated $NH_4Cl$ solution. After extraction of the aqueous phase with a suitable organic solvent, the organic phase is dried. The crude product can be purified by recrystallization, distillation or column chromatography.

It is advisable for the solvents used in this reaction to be predried. In principle, all conceivable organometallic compounds can be reacted with III.

The reduction of the hydroxylamines of the type IV to give the amines of the general formula V can be carried out in a manner known per se and analogously to Houben-Weyl, vol. 11/1, p. 341 et seq. Organic acids, such as, for example, acetic acids, inorganic acids, such as, for example, HCl, or organic solvents, such as acetonitrile, alcohols, ethers, esters, hydrocarbons, $CS_2$, can be employed here as solvents, depending on the reduction process used. The reaction temperature is between −20° C. and +120 ° C., preferably between +20° C. and +60° C. The reducing agent can be added in more than the stoichiometric (>1 equivalent based on IV), stoichiometric (1 equivalent based on IV) and in catalytic amounts.

Commercially available catalysts, such as, for example, Pd/C, Rh/$Al_2O_3$, Pt/C, Raney nickel, Raney cobalt, copper chromite, platinum oxide, palladium hydroxide, can be employed for the catalytic reduction. The hydroginolytic reduction can be carried out under normal pressure or pressures up to 50 atm.

The reduction is preferably carried out in the presence of $CS_2$, zinc or hydrogenolytically with Pd/C, Pt/C or Ra-Ni. Catalytic hydrogenation with Pd/C in hydrochloric acid solution under normal pressure at room temperature, optionally with the addition of ethanol, is particularly preferred.

Alternatively, cyclic imino acids, such as, for example, cis-4-hydroxyproline, are obtained via a cycloaddition on to compounds of the type III. In principle, both electron-rich and electron-poor dipolarophiles are suitable for the cycloaddition (see Houben Weyl "Methoden der Organischen Chemie [Methods of Organic Chemistry]" vol. E16a, p. 327 et seq., vol. E21c, p. 2953 et seq., vol. 14b, p. 1523 et seq. and the reaction conditions mentioned therein).

The reaction with electron-rich dipolarophiles, such as, for example, acrolein acetal, is preferably achieved in inert organic solvents, such as, for example, toluene, xylene, chlorobenzene or nitrobenzene, with subsequent reductive opening of the resulting isoxazolidine in a manner known per se (see Houben Weyl "Methoden der Organischen Chemie [Methods of Organic Chemistry]" vol. 10/1, p. 1256 et seq., Comp. Org. Synth. vol. 8 "Reduction" p. 648 et seq.) to give a compound of the type V where $R^2=CH_2CH(OH)CH(OR^5)_2$. These compounds of the general type V (in equation 1 type XVII as a specific form of the type V) can then have their protective groups removed by hydrolysis and be converted reductively (analogously to Bull. Chem. Soc. Jpn, vol. 54, p. 3871 (1981)) in a manner known per se into compounds of the type XVIII, before the compounds of the type XVIII are converted by hydrolysis (according to J. Chem. Soc. Chem. Commun. 11, 1291 (1994)) into a hydroxyproline derivative. The reactions proceed in good yields and stereoselectively (see equation 1).

Equation 1:
(Various acrolein acetals can be employed)

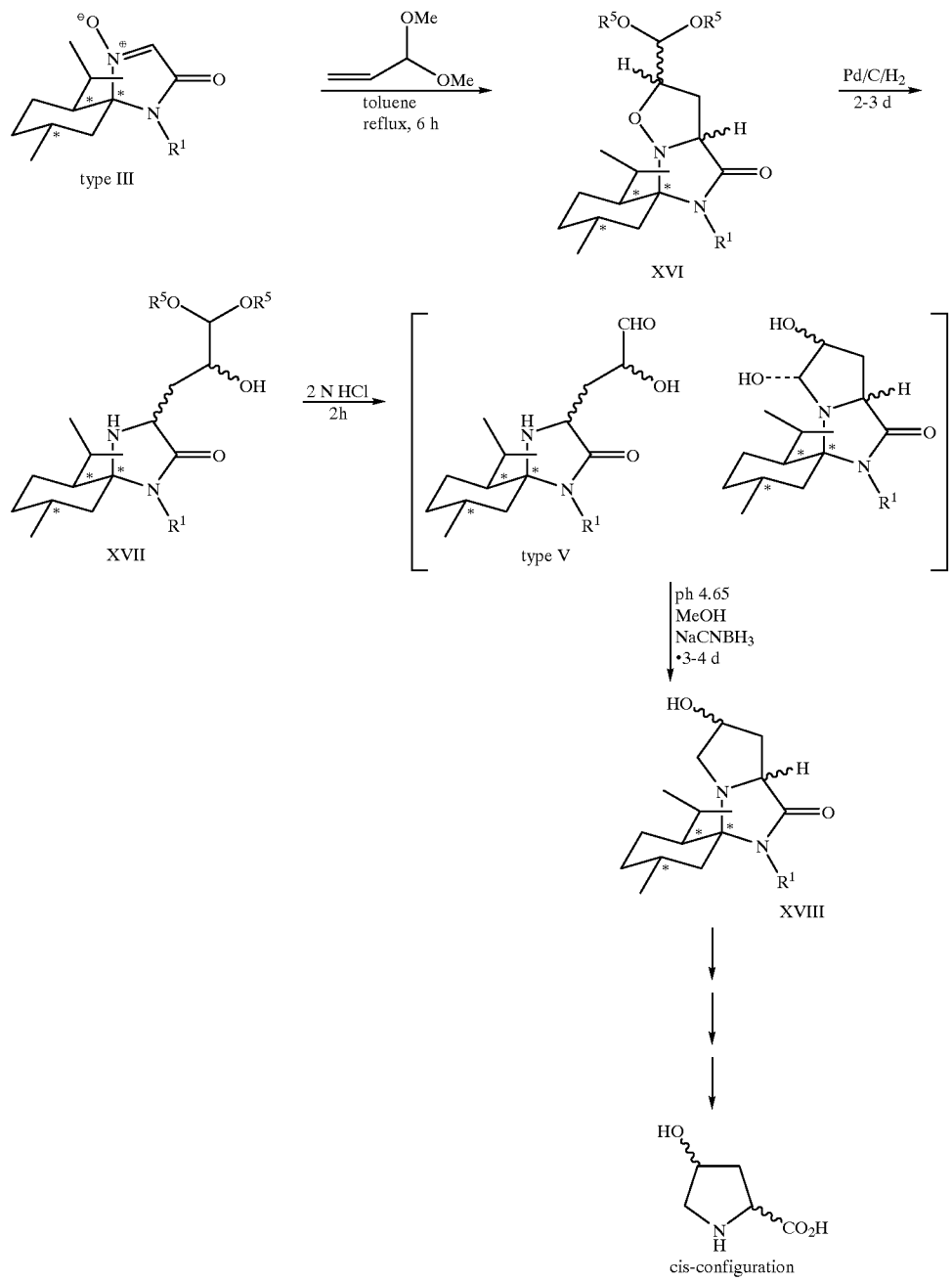

$R^5=CH_3$, $CH_2CH_5$ or together can form a 5-membered ring

One synthesis variant is 1,3-dipolar cycloaddition with allyl alcohol, which is illustrated in more detail in the following equation 2 and also gives a 4-hydroxyproline derivative.

Equation 2:

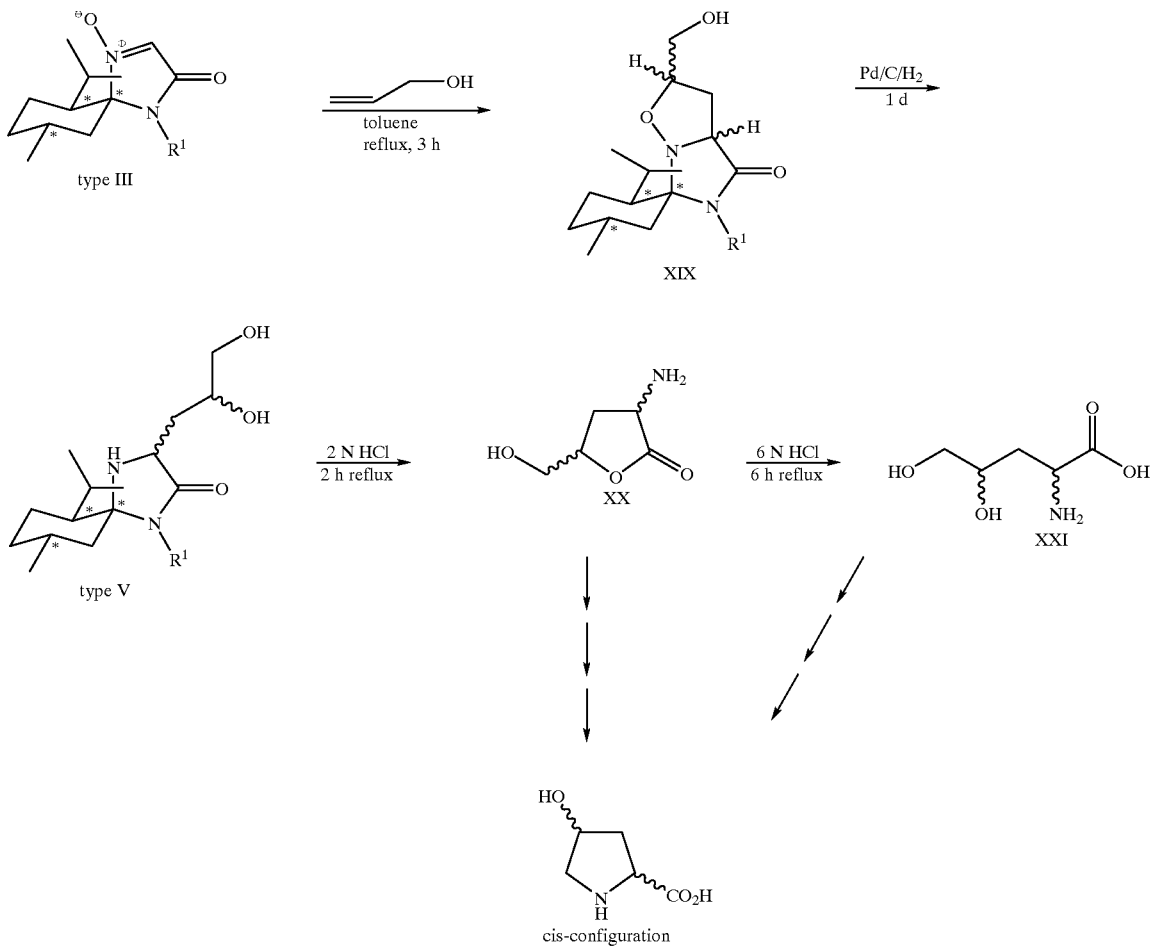

The synthesis of cis-4-hydroxyproline starting from the lactone XX or compound XXI is known (N. Kurokawa and Y. Ohfune in J. Am. Chem. Soc. 1986, 108, 6041–6043). The two variants shown for the 1,3-dipolar cycloadditions with the nitrones according to the invention are given by way of example and are not limited to these. Rather, by these the diversity of the building block according to the invention is demonstrated and the problem-free use and stereoselective reaction sequence explained. For both reaction equations, $R^1$ has the meaning already given above.

The hydrolysis of compounds of the general formula V to give the L- or D-amino acids or L- or D-amino acid derivatives I can be carried out analogously to D. Seebach, R. Fitzi, Tetrahedron 44 (1988) 5277 in an acid reaction medium, such as, for example, in the presence of an inorganic acid, such as HCl, HBr or $H_2SO_4$, and/or an acid cation exchanger and/or an organic acid, such as para-TsOH, camphorsulphonic acid, bromochamphorsulphonic acid or acetic acid, and/or an organic solvent, such as toluene or methanol. The reaction can be carried out at temperatures between 0° C. and 140° C., under normal pressure or also in an autoclave. The working up and isolation are carried out in the conventional manner and analogously to D. Seebach, R. Fitzi, Tetrahedron 44 (1988) 5277.

By a suitable reaction procedure, depending on the temperature and acid concentration, either optically active optionally substituted α-amino acid amides or the corresponding α-amino acids can be obtained (cf. D. Seebach, E. Juaristi, D. Muller, Ch. Schickli and Th. Weber, Helv. Chim. Acta, 70 (1987), 237

The compounds of the general formula I can also be present here in the form of an acid addition salt, such as, for example, as the HCl salt, HBr salt, $H_2SO_4$ salt, para-TsOH salt, camphorsulphonic acid salt, bromocamphorsulphonic acid salt or acetic acid salt, depending on the hydrolysis conditions chosen.

The reaction of compounds of the general formula IV to give compounds of the type VI is also carried out in a manner known per se analogously to Houben-Weyl "Methoden der Organischen Chemie [Methods of Organic Chemistry]", vol. 10/4, p. 315 et seq. Thus, for example, the compound IV is dissolved in an organic solvent, such as a halogenated hydrocarbon, such as methylene chloride, an aromatic hydrocarbon, such as toluene, an ether, such as THF, or in ethanol+aq. NH$_4$OH or glacial acetic acid, and reacted with an oxidizing agent, such as m-chloroperbenzoic acid, O$_2$+catalyst, H$_2$O$_2$, tert.-butyl hydroperoxide or potassium hexacyanoferrate (III). When the reaction has ended, conventional working up is carried out (cf. Houben-Weyl "Methoden der Organischen Chemie [Methods of Organic Chemistry]", vol. 10/4, p. 315 et seq.).

Alternatively, the building blocks V can be obtained by reaction of menthone and an amino acid ester in the presence of an amine component, such as, for example, methylamine, ethylamine, propylamine, benzylamine or isopropylamine, and a suitable organic solvent, such as, for example, an alcohol, such as methanol, ethanol, isopropanol, propanol, n-butanol, tert.butanol or sec.butanol. The compounds of the type V thus obtained can then be converted into compounds of the type VI by oxidation analogously to the oxidation of the compound type II to give compound type III.

Alternatively, the compounds of the type IV can also be obtained directly from compounds of the type III. For this, the compounds of the type III are reacted with a substituted carboxylic acid, such as R$^2$CO$_2$H, wherein R$^2$ has the meaning already given, with a free-radical initiator, such as, for example, dibenzoyl diperoxide, azobisisobutyronitrile, K$_2$S$_2$O$_8$/AgNO$_3$ or PhI(CF$_3$CO$_2$)$_2$ (see also Houben-Weyl "Methoden der Organischen Chemie [Methods of Organic Chemistry]", vol. E19a, part 1, p. 140 et seq.) in an organic solvent, such as a halogenated hydrocarbon, such as methylene chloride, chloroform or dichloroethane, an inert aromatic hydrocarbon, such as benzene, toluene, xylene, chlorobenzene, nitrobenzene, optionally with heating of the reaction mixture to 30° C. to 160° C., preferably to 70° C.–140° C. The reaction is monitored by means of thin layer or gas chromatography. The reaction is carried out under an inert gas atomsphere, i. e. for example under a nitrogen or argon atmosphere.

The further reaction of compounds of the type VI to give compounds of the type VII is carried out analogously to the reaction of III to give IV, at temperatures between +80° C. and −50° C., preferably at +25 ° C. to −25° C., particularly preferably at 0° C., and preferably with toluene as the solvent.

The further reactions of compounds of the type VII to give VIII and VIII to give I are carried out analogously to the reactions of IV to give V and V to give I (L- or D-amino acids, L- or D-amino acid derivatives) according to D. Seebach et al., Liebigs Ann. 1995, 217.

In one variant of the process, the D-amino acids or D-amino acid derivatives or the L-amino acids or L-amino acids derivatives of the general formula I or of an acid addition salt thereof,

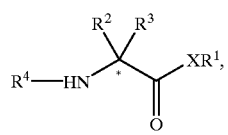

I wherein
*=centre of asymmetry
X =O or NH

R$^1$=H, (C$_1$–C$_6$) alkyl, benzyl or (C$_1$–C$_4$) alkoxycarbonylmethyl and R$^2$, R$^3$, independently of one another, denotes H, (C$_1$–C$_6$) alkyl, which can be interrupted or substituted by heteroatoms, such as N, P, O, S or Si, it being possible for the heteroatoms themselves to be substituted by (C$_1$–C$_3$) alkyl once or several times, (C$_2$–C$_6$) alkenyl, (C$_1$–C$_6$) haloalkyl, halogen, aryl, such as naphthyl or phenyl, which can be substituted by (C$_1$–C$_3$) alkyl, hydroxyl, halogen or (C$_1$–C$_3$) alkoxy once or several times, aralkyl, such as 2-naphthylmethyl or benzyl, which in its turn can be substituted by (C$_1$–C$_3$) alkyl, hydroxyl, halogen or (C$_1$–C$_3$) alkoxy once or several times, heteroaralkyl, such as N-protected 3-indolylmethyl, and

R$^4$=H, wherein if R$^2$=H, R$^3$≠H, are prepared by a procedure in which a) the compounds of the general formulae IX and X

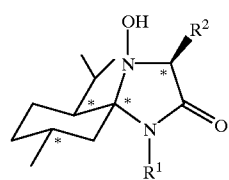

IX

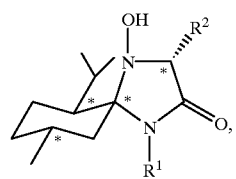

X wherein *, R$^1$ and R$^2$ have the meaning already given, b) are dehydrated to give compounds of the general formula XI

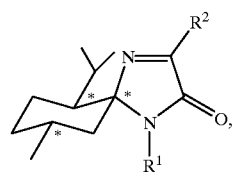

XI wherein *, R$^1$ and R$^2$ have the meaning already given, and the compounds of the general formula XI are then inverted by reduction, so that finally compounds of the type XII arise from compounds of the type IX finally compounds of the type XIII arise from compounds of the type X (see equation 1.

Equation 3:

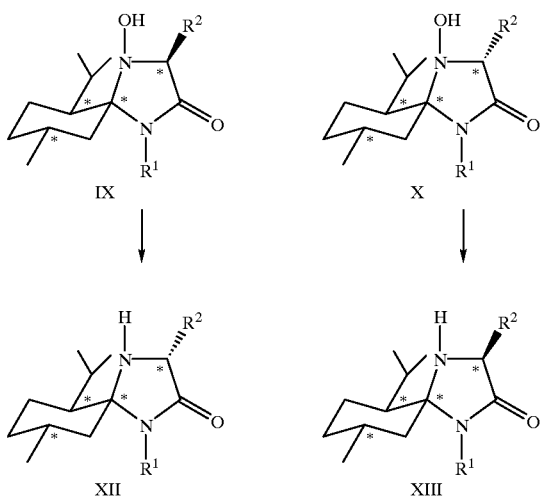

before the compounds of the general formulae XII and XIII are hydrolysed to give the amino acids or amino acid derivatives of the general formula I or of an acid addition salt thereof.

The dehydration of the compounds IX and X to give XI can be carried out in a manner known per se (Houben-Weyl "Methoden der Organischen Chemie [Methods of Organic Chemistry]", vol. 10/1, p. 1247, vol. E16a, p. 211 et seq.). Thus, for example, the hydroxylamine compound of the type IX or X is stirred in an organic solvent, such as methylene chloride, pyridine, ether, in the presence of a dehydrating agent, such as N,N'-carbonyldiimidazole, DCC or $P_2O_5$, with exclusion of air (e. g. $N_2$ atmosphere or argon atmosphere) at temperatures of between 0° C. and 120° C., preferably between 20° C. and 30° C., and, when the reaction has ended, the mixture is worked up.

The compounds of the general structure type XI can then be converted into the compounds of the type XII and XIII under reducing conditions with inversion of configuration. The reduction can be carried out analogously to the reduction already described for compounds of the type IV to give V. Catalytic hydrogenation with $Pd(OH)_2/C$ in ethanol at 25° C. under normal pressure is preferred (cf. also B. Trost, I. Fleming, Compr. Org. Syn., vol. 8, "Reductions", Pergamon Press, Oxford 1991).

The subsequent hydrolysis of the compounds of the type XII and XIII to give compounds of the type I is carried out analogously to that described for V to give I.

Compared with a deprotonation-reprotonation sequence, such as is typically carried out on glycine α-anion equivalents for inversion of configuration (LDA, THF, −78° C.,>92% Inversion, D. Seebach, E. Dziadulewicz, L. Behrendt, S. Cantoreggi and R. Fitzi, Liebigs Ann. Chem. 1989, 1215), a dehydration-hydrogenation sequence in the course of the glycine α-cation route of the process according to the invention on the other hand also advantageously already leads highly selectively (ee>99%, GC) into the corresponding enantiomeric series of the amino acids (ee= 99%) at room temperature in ethanol.

The new process is explained once more by a reaction equation in the following:

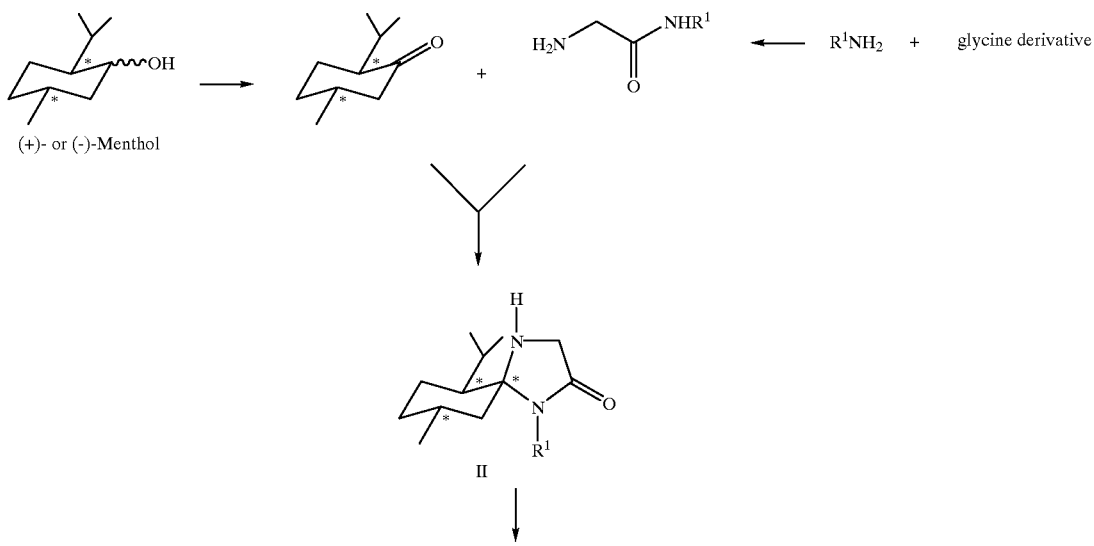

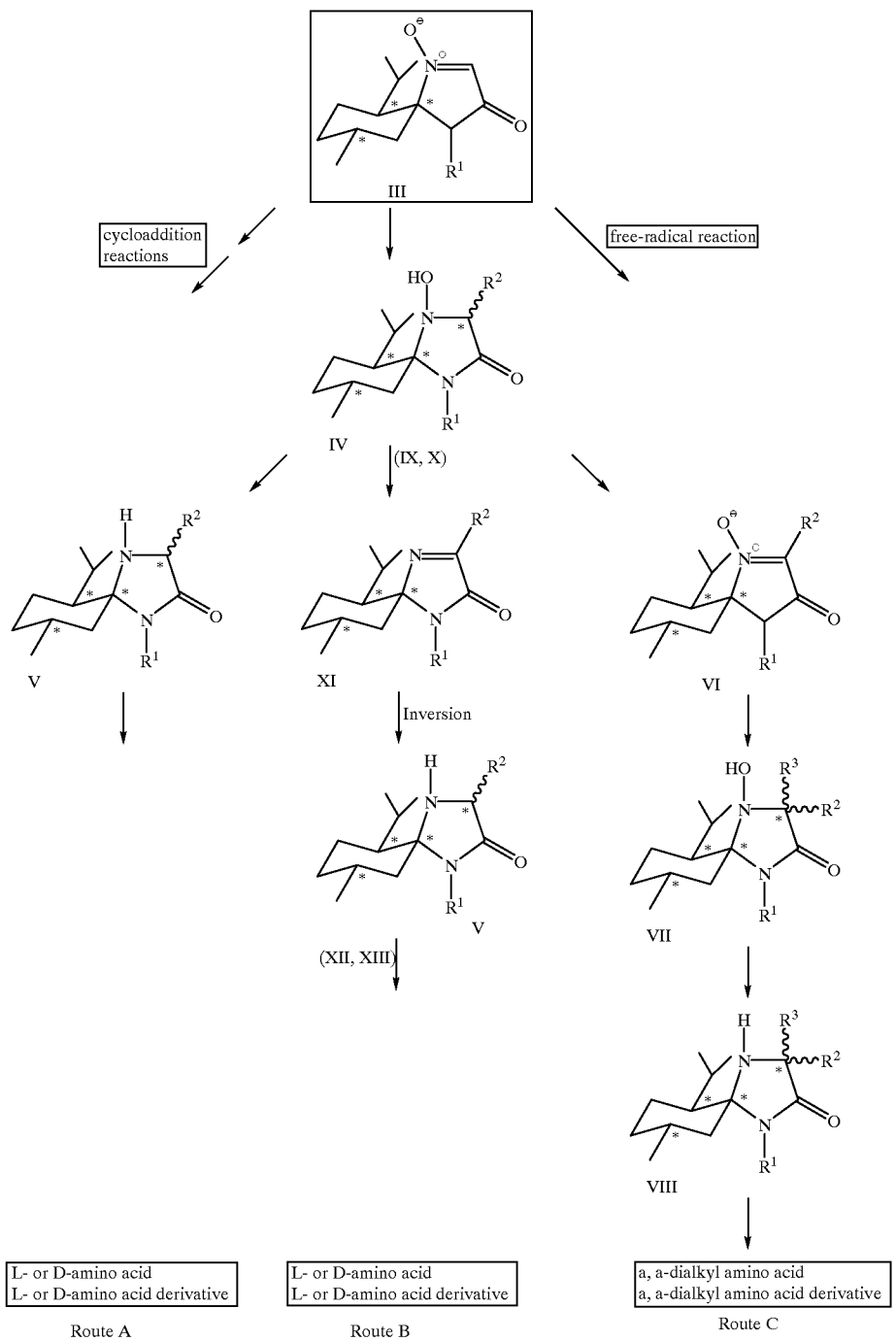

Route A
L- or D-amino acid
L- or D-amino acid derivative

Route B
L- or D-amino acid
L- or D-amino acid derivative

Route C
α,α-dialkyl amino acid
α,α-dialkyl amino acid derivative

Depending on the choice of the appropriately configured menthol as the starting substance, the corresponding configured amino acids and their derivatives can advantageously be obtained in the process according to the invention. Thus, starting from (−)-menthol, the L-configured species is obtained, while the corresponding D-configured species can be obtained with (+)-menthol. The amino acids and the amino acids derivatives are obtained here in good chemical yields and high stereochemical purities of in some cases >99%.

The compounds of the general formula IV are compounds which have a very high enantiomer excess.

Alternatively, in the process according to the invention, via the intermediate stage XI, it is possible to enter into the series of D-amino acids or D-amino acids derivatives starting from (−)-menthol and to enter into the series of L-amino acids and L-amino acids derivatives starting from (+)-menthol.

Furthermore, α,α-dialkylamino acid or α,α-dialkylamino acids derivatives can be prepared via the intermediate stages VI, VII and VIII.

Also advantageously, menthone is volatile in water vapour and, after liberation of the amino acids, can be separated off and recycled particularly easily as a chiral auxiliary.

Another advantage of the process is that the starting substances (+)-menthol and also (−)-menthol are commercially obtainable without problems at favourable and similar prices.

In another variant, it is possible with the process according to the invention to propane N-hydroxy-amino acids of the general formula I

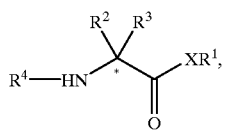

I wherein
*=centre of asymmetry
X=O, or NH
R=H, $(C_1-C_6)$ alkyl, benzyl or $(C_1-C_4)$ alkoxycarbonylmethyl and
$R^2$ $R^3$ independently of one another, denotes H, $(C_1-C_6)$ alkyl, which can be interrupted or substituted by heteroatoms, such as N, P, O, S or Si, it being possible for the heteroatoms themselves to be substituted by $(C_1-C_3)$ alkyl once or several times, $(C_2-C_6)$ alkenyl, $(C_1-C_6)$ haloalkyl, halogen, aryl, such as naphthyl or phenyl, which can be substituted by $(C_1-C_3)$ alkyl, hydroxyl, halogen or $(C_1-C_3)$ alkoxy once or several times, aralkyl, such as 2-naphthylmethyl or benzyl, which in its turn can be substituted by $(C_1-C_3)$ alkyl, hydroxyl, halogen or $(C_1-C_3)$ alkoxy once or several times, heteroaralkyl, such as N-protected 3-indolylmethyl, and
$R^4$=OH, wherein if $R^2$=H, $R^3 \neq H$, by a procedure in which compounds of the general formula IV

IV

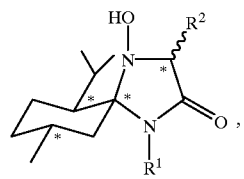

are reacted with an organometallic reagent, optionally in the presence of a solvent, to give compounds of the formula XIV

XIV

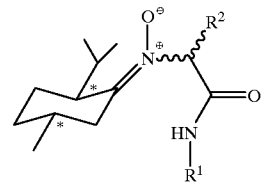

and XIV is then reacted further, optionally in the presence of a solvent and optionally in the presence of an acid, to give compounds of the type I.

The chain tautomers of the general structure XIV can be obtained in a targeted manner by reaction of IV with an organometallic (see above) compound. The use of methylmagnesium and the reaction conditions described on compounds of the type IV in the following equation 4 is given by way of example. $R^1$ and $R^2$ have the meaning already given above.

Equation 4

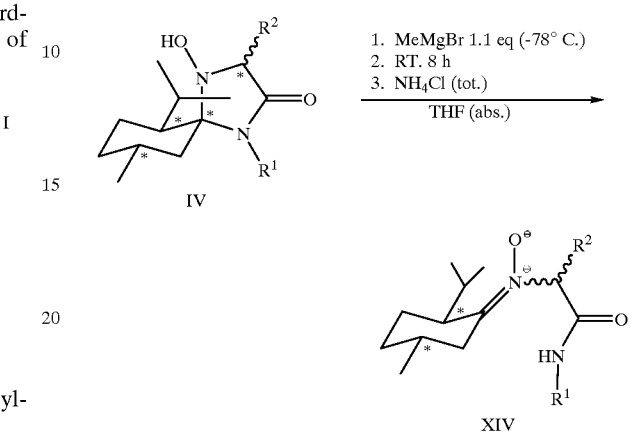

Under controlled conditions, a ring opening of IV to give the chain tautomer nitrone XIV can be carried out in good yields by addition of 1.0–5.0 equivalents, preferably 1.0–1.5 equivalents, of an organometallic reagent in an organic solvent, for example an ether, such as methyl tert.butyl ether or THF, to compounds of the type IV at temperatures of between +30° C. and −100° C., preferably 0° C. and −80° C. To avoid an epimerization in the α-position to the amide function, particular care should be taken that the solution of the Grignard reagent is also precooled to −78° C. and the rate of dropwise addition is not too rapid.

The open-chain nitrones are formed as a mixture of E/Z isomers. The ring-opening reaction proceeds stereoselectively.

The compounds of the type XIV can be isolated or can also subsequently be hydrolysed in situ to give the N-hydroxyamino acids. The hydrolysis can be carried out in accordance with OpDholzer et al., Helv. Chim. Acta 75 (1992), 1965. If mild hydrolysis conditions are used, the corresponding precursors of the N-hydroxyamino acids, that is to say the N-hydroxyamino acid amides x HCl (I, $R^4$=OH), can also be obtained. For this, hydrochloric acid is preferably used, in concentrations of 0.1 N to 2 N, particularly preferably 0.5 N. The following equation 5 illustrates the reaction by way of example.

Equation 5

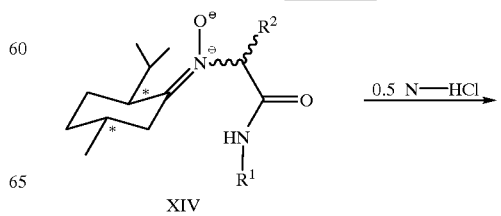

XIV

-continued

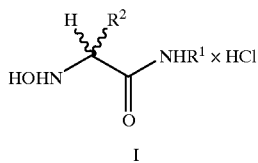

I

In principle, depending on the choice of the starting conditions, N-hydroxyamino acid derivatives in the various configurations (L or D) can be obtained in this way.

The invention is to be illustrated in more detail with the aid of the following embodiment examples, but is not limited to these. The compounds shown in tables I to VIII were prepared analogously to examples 1–11, some of which contain general working instructions.

EXAMPLES

1. Synthesis of (SR,6S,9R)-6-isopropyl-1,9-dimethyl-1,4-diazaspiro[4.5]decan-2-one (type II)

156 ml of a commercially obtainable 8M ethanolic methylamine solution are added to 62.8 g glycine.imethyl ester hydrochloride (500 mmol) in 160 ml ethanols. at room temperature and the mixture is stirred overnight with exclusion of moisture. 40.5 g triethylamine (400 mmol) and 61.6 g (−)-menthone (400 mmol) are then added to the suspension and the mixture is boiled under reflux for 18 h under an inert gas (argon) using a Soxhlet attachment which is filled with 100 g molecular sieve 3A (capacity: 14%). Thereafter, the solvent is removed and the residue is taken up in a two-phase system of water/diethyl ether. After the organic phase has been separated off, extraction is carried out twice more with diethyl ether and the extract is dried over sodium sulphate. After the yellow solution has been evaporated, the residue can be recrystallized from cyclohexane/diethyl ether =8:2. During distillation of the mother liquor in vacuo, the content of the desired compound can be increased by cyclizing the chain tautomer. Unreacted menthone passes over as the first fraction (70° .C/1 mbar), followed by a mixture of the desired product and chain tautomer (140–150° C., 1 mbar). After cyclohexane has been added to the product fraction, further product can be obtained as a crystalline solid with a melting point of 125° C. The yield is 65%.

2. Synthesis of (5S,6S,9R)-6-isopropyl-4,9-dimethyl-1,4-diazaspiro[4.5]dec-1-en-3-one 1-oxide (type III) 22.4 g (5R, 6S,9R)-6-isopropyl-1,9-dimethyl-1,4-diazaspiro[4.5]decan-2-one (type II) (100 mmol) in 600 ml $CH_2Cl_2$ are reacted with three portions (2.5 equivalents in total, ~70 g) of aqueous m-CPBA (Aldrich) in an ice-bath in the course of three hours. The white suspension is stirred for a total of 5 h at 0° C. (monitoring by GC). When the conversion is complete, a 10% $Na_2S_2O_3$ solution is added for reduction of excess peracid and the phases are mixed thoroughly by vigorous stirring for 1 h. Thereafter, 200 ml saturated $NaHCO_3$ solution are added. When the evolution of $CO_2$ has ended, the organic phase is separated off and the aqueous phase is extracted twice more with $CH_2Cl_2$. The combined methylene chloride phases are washed with sat. $NaHCO_3$ solution, dried over sodium sulphate and evaporated. The crude product is already present in a very pure form and can be recrystallized from diethyl ether. (Yield: 94%, m.p.: 133.5° C.).

3. Reactions of (5S,6S,9R)-6-isopropyl-4,9-dimethyl-1,4-diazaspiro[4.5]dec-1-en-3-one 1-oxide (type III) with organometallic reagents to give type IV a) 4.76 g (5S,6S,9R)-6-isopropyl-4,9-dimethyl-1,4-diazaspiro[4.5]dec-1-en-3-one 1-oxide (type III) (20 mmol) are dissolved in 400 ml diethyl ether$_{aba}$ and the solution is cooled to −50° C. under argon. 2.5 equivalents of a 1 M Grignard solution or solution of an organometallic reagent are slowly added dropwise, while stirring thoroughly, and the suspension formed is subsequently stirred at −50° C. (monitoring by TLC). After warming to −20° C., the mixture is poured all at once into 250 ml of an ice-cold half-saturated $NH_4Cl$ solution, good thorough mixing being ensured. After separation of the phases, extraction is carried out twice more with diethyl ether and the combined organic phases are dried over sodium sulphate. The crude product is obtained in a diastereomerically pure Form by column chromatography or recrystallization.

b) 16.0 g (5S,6R,9R)-6-isopropyl-4,9-dimethyl-1,4-diazaspiro[4.5]dec-1-en-3-one 1 oxide (type III) (67 mmol) are dissolved in 600 ml tolueneab. 2.5 equivalents of a 1M Grignard solution are added dropwise in an argon atmosphere at −15° C. in the course of 2.5 h (monitoring by TLC after the addition has ended). After warming to 0 C, the suspension is poured into an ice-cold half-saturated $NH_4Cl$ solution, while stirring vigorously. After the aqueous phase has been separated off, this is extracted twice more with toluene and the combined organic phases are dried over sodium sulphate. After removal of the solvent in vacuo, the product is obtained by column chromatography or recrystallization.

4. Reduction of the hydroxylamines (type IV) to give the secondary amines (type V)

a) Deoxygenation with carbon disulphide 3 mmol of the hydroxylamine are dissolved in 80 ml acetonitrileab, and the solution is stirred with 18 ml $CS_2$ (300 mmol) at room temperature under an inert gas for several days. During this period, the sulphur formed precipitates out as a flocculent precipitate. The reaction is monitored by gas chromatography by observing the increase in the product peak (the educt decomposes under these conditions!). If necessary, further $CS_2$ must be added to bring the reaction to completion. When the reaction has ended, the entire mixture is evaporated on a rotary evaporator and the residue is taken up in a little methanol, the sulphur remaining as a yellow powder. After filtration and evaporation of the solution, the product can be purified by column chromatography over silica gel RP-18.

b) Reduction with zinc 1 mmol substance is suspended in 8 ml 50% acetic acid and the suspension is heated to 60° C., the educt dissolving completely. 1.70 g zinc dust are introduced into the hot solution in two portions, while stirring thoroughly. After 30 minutes, the progress of the reaction is checked by gas chromatography and, optionally, the reaction time is extended. After discontinuation of the reaction, the zinc is filtered off and the filtrate is extracted with methylene chloride under acid conditions. The organic phase is washed with half-saturated $NaHCO_3$ solution, dried over sodium sulphate and evaporated in vacuo.

c) Hydrogenolysis with Pd/C 76 mg catalyst (DEGUSSA, E 101 R/W 10%, water content 51%) are prehydrogenated under 1 atm $H_2$ in 20 ml 1 N HCl at room temperature. Thereafter, 2 mmol of the crystalline hydroxylamine are added via a Schlenck tube. A suspension is initially present, and clarifies overnight during the course of the reaction. After discontinuation of the reaction, the flocculent catalyst is filtered off and the hydrochloric acid solution is evaporated at 30° C. under a water pump vacuum. The product is as a rule already present in a very pure form. By rendering basic with saturated $NaHCO_3$ solution and taking up in ethyl acetate, product samples can be analysed by gas and thin layer chromatography.

5. Dehydration of the hydroxylamines to give ketimines (type XI)

3.4 mmol hydroxylamine compound are dissolved in 50 ml $CH_2Cl_2$ $_{aba}$. 0.84 g N,N'-carbonylimidazole is added at room temperature and the clear solution is stirred in an argon atmosphere for 6 h (yellow coloration). When the reaction has ended (monitoring by GC), 30 ml 0.25 N HCl are added and the mixture is extracted twice more with $CH_2Cl_2$. The combined organic phases are washed with saturated $NaHCO_3$ solution and dried over sodium sulphate. The resulting crude oils, which already have a high purity, can be chromatographed over silica gel.

6. Hydrogenation of the ketimines to give the secondary amines (inversion of the stereo-centre) 2 mmol ketimine are dissolved in 25 ml $EtOHb_{,,}$ and 125 mg $Pd(OH)_2/C$ (Aldrich, ~20%) are added. After hydrogenation overnight (1 atm $H_2$, room temperature), the secondary amine is converted into its hydrochloride by addition of 4 ml 1 N HCl. By addition of water in portions, a flocculent precipitate which can be filtered off without problems is obtained from the very finely divided catalyst. After evaporation of the filtrate under a water pump vacuum at 30° C., the product is present as a pulverulent solid. Alternatively, when the hydrogenation has ended and after addition of a little dimethyl sulphide (150 ml=2 mmol), the ethanolic solution can be filtered through Celite and the filtrate can be evaporated on a rotary evaporator. The free secondary amine is obtained as a waxy or oily substance.

7. Reoxidation of the hydroxylamines to give the nitrone (type VI) (synthesis of (5S,6S,9R)-2-ethyl-6-isopropyl-4,9-dimethyl-1,4-diazaspiro[4.5]-dec-1-en-3-one 1-oxide)

1.70 g hydroxylamine (3S,5S,6S,9R)-3-ethyl-4-hydroxy-6-isopropyl-1,9-dimethyl-li4-diazaspiro[4.5]-decan-2-one (6.3 mmol) are dissolved in 50 ml $CH_2Cl_2$ and reacted with 2.77 g m-CPBA (8.8 mmol, 55%) in an ice-bath. After 2 h, 25 ml of a 10% $Na_2S_2O_3$ solution and then 40 ml saturated $NaHCO_3$ solution are added, with vigorous thorough mixing, and when the evolution of $CO_2$ has ended, the mixture is extracted by shaking. After the organic phase has been separated off, extraction is carried out twice more with $CH_2Cl_2$ and the combined organic phases are washed with saturated $NaHCO_3$ solution. After drying over sodium sulphate and removal of the solvent in vacuo, a yellow oil is present, which is chromatographed over silica gel (cyclohexane/ethyl acetate =7 : 3) to give 67% of the desired product.

(Optical rotation: $[\alpha]_D$=+24.50 ($CHCl_3$, c=0.75))

8. Preparation of the compounds of the type V from amino acid esters 32 ml of a commercially obtainable 8 M ethanolic methylamine solution are added to 0.1 mol amino acid methyl esterehydrochloride, dissolved in 50 ml $ethanol_{abs}$ or n-butanol, at room temperature. After the suspension has been stirred overnight under an inert gas, 0.1 mol triethylamines$_3$ and 0.1 mol menthone are added. The reaction mixture is boiled under reflux for 48 h using a Soxhlet attachment filled with 20 g molecular sieve 3 Å (capacity: 14% at 23 ° C.). In the middle of the reaction time, the molecular sieve is replaced to achieve as complete as possible a reaction. The solvent is removed and the yellow to brown residue is taken up in a two-phase system of diethyl ether/water. After the organic phase has been separated off, extraction is carried out three more times with diethyl ether, the combined organic phase is dried over magnesium sulphate and the solvent is evaporated off.

9. Reactions of the compounds of the type III to give compounds of the type VI using the example of 2-tert. butyl-6-isopropyl-4,9-dimethyl-1,4-diazaspiro[4.5]-dec-1-en-3-one 1 oxide (direct route; free-radical reaction)

The solvent mixture (12.5 ml $H_2O$, 12.5 ml 1,2-dichloroethane) is degassed thoroughly, the reactants 250 mg (1.05 mmol) nitrone, 321 mg (3.15 mmol; 3 eq) pivalic acid, 425 mg (1.58 mmol; 1.5 eq) $K_2S_2O_8$ aid 150 mg (1.05 mmol) $AgNO_3$ are dissolved in the sequence listed and the solution is boiled under reflux under an inert gas atmosphere. The course of the reaction is monitored by means of thin layer and gas chromatography and the reaction is continued until virtually no further educt can be detected. Optionally, the course of the reaction can be accelerated towards the end of the reaction by subsequently metering in potassium peroxodisulphate and silver nitrate several times up to a maximum ratio of 10 and 5 equivalents respectively, based on the nitrone employed. For working up of the mixture, the aqueous phase is separated off and the organic phase is extracted three times by shaking with 20 ml sat. $NaHCO_3$ solution each time. The combined aqueous phases are shaken twice against 25 ml methylene chloride and the organic phases are combined, dried over $MgSO_4$ and evaporated on a rotary evaporator. The crude product obtained after complete removal of the solvent on a high vacuum rotary evaporator is purified by column chromatography (silica gel SG 60, mobile phase cyclohexane/isopropanol 9/1). 209 mg (0.71 mmol; 68%) of the desired product are obtained as a yellowish oil.

10. Total hydrolysis of the secondary amines to give the free amino acids 1 mmol secondary amine is introduced into a conical flask together with 10 ml 0.75 N HCl, 0.75 ml glacial acetic acid, 1.5 mol toluene and 10 ml DOWEX 50 W×8 strongly acid cation exchanger (20–50 mesh). This flask is closed with a greased glass stopper and secured with a steel clamp. The mixture is heated at 105 ° C. in an oil bath for 20 h (the reaction is monitored by thin layer chromatography by removal of a little ion exchanger resin and elution with 10% NH3 solution, mobile phase: utanol/$H_2O$/HOAc=3:1:1). After discontinuation of the reaction, the ion exchanger resin is transferred to a lass column and rinsed successively with ethanol (50 ml) and $H_2O$ until neutral. It is then rinsed with 10% $NH_3$ solution until samples of eluate give a negative ninhydrin reaction on silica gel plates. After evaporation of the aqueous solution under a water pump vacuum, the solid residue is twice more dissolved in a little $H_2O$ the solution is evaporated on a rotary evaporator and the residue is dried under a high vacuum. The white powder is twice heated to the boiling point in $acetone_{abs}$ and, after cooling, decanted. The amino acid thus obtained in the residue is tested for enantiomer purity.

11. Partial hydrolysis of the secondary amines of the type V or VIII, by the example of (2S)-2-amino-4-phenylbutyric acid methylamide by way of example 0.80 g (2.4 mmol) (3S,5R,6S,9R)-6-isopropyl-1,9-dimethyl-3-phenethyl-1,4-diazaspiro-[4.5]decan-2-one is emulsified in 40 ml 5% HCl and the emulsion is heated under reflux for 2 h. After cooling, the menthone which has been split off is extracted with 2 x 20 ml ether, the aqueous phase is evaporated on a rotary evaporator and the residue is dried on a high vacuum apparatus. The polar crude product is purified by column chromatography (CH$_2$Cl$_2$/MeOH=13/7).

Yield: 0.35 g (75%) colourless crystals

R$_f$: 0.25 (CH$_2$Cl$_2$/MeOH=13/7)

Optical rotation: [a]D =+42.51° (c =1, in MeOH)

$^1$H-NMR spectrum (CD$_3$OD): δ(ppm)=7.41-7.13 (m, 5 H, phenyl 30 protons); 3.94 (dd, 1 H α-position proton, J=6.3 Hz); 2.78 (s, 3 H, N—CH$_3$); 2.70 (dd, 2 H, benzylic protons, J=8.4 Hz); 2.13 (m, 2 H, β-position protons).

The structures illustrated in the tables for the most part represent the absolute configuration.

TABLE I

Synthesis of compounds of the type IV

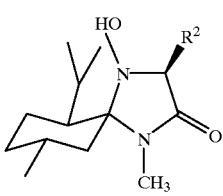

| R$^2$ | Yield in % | M.p. in ° C. |
|---|---|---|
| a) starting from (−)-menthol | | |
| CH=CH$_2$ | 73 | 94.2 |
| CH(CH$_3$)$_2$ | 39 | 134.1 |
| C(CH$_3$)$_3$ | 60$^{\alpha)}$ | 171.8 (decomposition) |
| CH$_2$C$_6$H$_5$ | 71 | 132.6 |
| CH$_3$ | 83 | 175.5 |
| C$_5$H$_5$ | 77 | 96.8 |

α) with precooled tert. butyllithium as the organometallic reagent and THF as the solvent b) starting from (+)-menthol

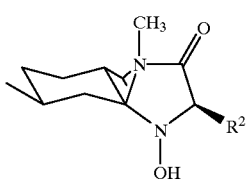

| C$_6$H$_5$ | 26 | 52.7 |
| p-Br—C$_6$H$_4$ | 11 | oil |
| (CH$_3$)$_2$CH$_2$—CH$_2$ | 52 | 116.3 |

TABLE II

Synthesis of compounds of the type V a) starting from (−)-menthol

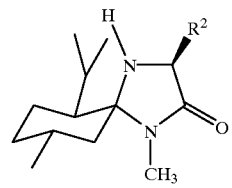

| R$^2$ | Yield in % | Optical rotation [α]$_D^{20}$, CHCl$_3$ |
|---|---|---|
| CH$_3$ | 58$^{a)}$/90$^{b)}$/95$^{c)}$ | +8 |
| CH$_2$CH$_3$ | 72$^{a)}$/98$^{c)}$ | −2.2 (c = 3) |
| CH(CH$_3$)$_2$ | 78$^{a)}$/100$^{b)}$/97$^{c)}$ | −6 (c = 0.9) |
| C(CH$_3$)$_3$ | 96$^{d)}$ | −6 (c = 0.5) |

$^{a)}$Reaction according to GWI 4a;
$^{b)}$Reaction according to GWI 4b;
$^{c)}$Reaction according to GWI 4c; the compounds are obtained as the HCl salt;
$^{d)}$Reaction according to GWI 4c and addition of ethanol. Yield based on free sec. amine after rendering basic and extracting with organic solvent.

b) starting from (+)-menthol

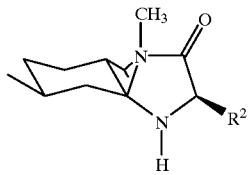

| R$^2$ | Yield in % | Optical rotation [α]$_D^{20}$, c = 0.05, CHCl$_3$ | Melting point in ° C. |
|---|---|---|---|
| C$_6$H$_5$ | 15 | −1.2 | 145.1 |

TABLE III

Synthesis of compounds of the type XI from V (starting from (−)-menthol)

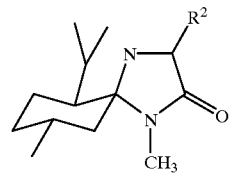

| R$^2$ | Yield in % | Optical rotation [α]$_D^{20}$, CHCl$_3$ |
|---|---|---|
| CH=CH$_2$ | 80 | +27.5 (c = 1) |
| CH(CH$_3$)$_2$ | 16 | +5.7 (c = 0.85) |
| CH$_3$ | 93 | +7.8° (c = 3.7) |
| C$_2$H$_5$ | 63 | +5.7° (c = 1.5) |
| (CCH$_3$)$_3$ [sic] | 64 | α) |

α) $^1$H-NMR (400 MHZ, CDCl$_3$): δ = 2.84(s, 3H, CH$_3$-15); 2.10–0.58: menthyl, isopropyl and tert-butyl protons 27 H, in these: 1.34(s, 9H. C(CH$_3$)$_3$); 0.92(d, 3H, $^3$J = 6.6 Hz, CH$_3$-11): 0.84(d, 3H, $^3$J = 6.9 Hz, CH$_3$-13/14); 0.59(d, 3H, $^3$J = 6.8 Hz, CH$_3$-14/13)

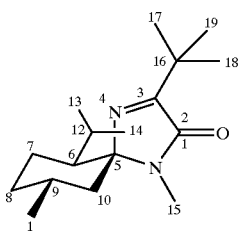

TABLE IV

Synthesis of compounds of the type VI 1. from compounds of the type IV
a) starting from (−)-menthol

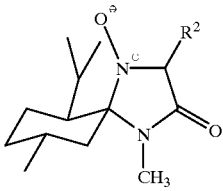

| $R^2$ | Yield in % | Optical rotation $[\alpha]_D^{20}$, CHCl$_3$ |
| --- | --- | --- |
| CH$_2$CH$_3$ | 67 | +24.5° (c = 0.75) |
| CH$_3$ | 98 | +94.4° (c = 2.7) |
| C(CH$_3$)$_3$ | 68 | α) |

α) $^1$H-NMR(400 MHZ, CDCl$_3$): δ = 2.87(s, 3H, N—CH$_3$); 2.70(m,1H, H$_{ax}$ at C7); 2.2–1.4(m, 8H, menthyl protons, CH(C12); 1.44(s, 9H, CH$_3$ t-butyl); 0.93(d; 3H, $^3$J = 6.63 Hz, CH$_3$(C11); 0.92(d, 3H, $^3$J = 6.88 Hz, CH$_3$(C13/14); 0.75(d, 3H, $^3$J = 6.78 Hz, CH$_3$(C13/14)

$^{13}$C-NMR (100.6 MHZ CDCl$_3$) : δ=163.47 (s, C-3) ; 141.03 (s, C-2); 88.43 (s, C-5); 46.51 (d, C-6); 43.41(t, C-10) ; 34.22 (t, C-8) ; 33.38 (s, C-16) ; 27.18 (d, C-9): 26.33 (q, C-17,17,17) ; 24.67 (q, C-15); 24.21 (d, C-12) ; 23.79 (q, C-13/14) : 22.34 (q, C-ll); 20.11 (t, C-7); 17.05 (q, C-13/14)

b) starting from (+)-menthol

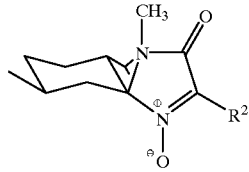

| $R^2$ | Yield in % | Optical rotation $[\alpha]_D^{20}$, CHCl$_3$ |
| --- | --- | --- |
| C$_6$H$_5$ | 96 | +7.85° (c = 0.26) |
| (CH$_3$)$_2$CH$_2$CH$_2$ | 89 | −35.9° (c = 0.93) |

2. from compounds of the type III (free-radical reaction) (see reaction instructions 9.)
a) starting from (−)menthol α) $R^2$=cyclohexyl yield: 58% (oil)
Bis-(trifluoroacetoxy)-iodo-benzene was used as the free-radical initiator and benzene was used as the solvent. Mobile phase: methylene chloride/methanol=99/1.
$^1$H-NMR (400 MHZ, CDCl$_3$): 2.89 (s, 3 H, N—CH$_3$); 2.67 (m, 1 H, H$_{ax}$ at C7); 2.3–1.0 (m, 13 H, menthyl protons, CH (C12), cyclohexyl protons); 0.92 (d, 3H, $^3$J =6.35 Hz, CH$_3$ (C11)); 0.91 (d, 3 H, $^3$J=6.82 Hz, CH$_3$ (C13/14)); 0.73 (d, 3 H, $^3$J =6.87 Hz, CH$_3$ (C13/14))

β) $R^2$=CH (CH$_3$)$_2$ yield: 48%
$^1$H-NMR (400 MHZ, CDCl$_3$): δ=3.17 (sept., 1 H, $^3$J =7.1 Hz, C-H (C 16)); 2.86 (s, 3 H, N-CH$_3$); 2.64 (m, 1 H, H$_{ax}$ at C7); 2.4-0.7 (m, 24 H, menthyl protons, isopropyl protons)

γ) $R^2$=C(CH$_3$)$_3$ yield: 68% (oil)
$^1$H-NMR (400 MHZ, CDCl$_3$): δ=2.87 (s, 3 H, N—CH$_3$); 2.70 (m, 1 H, Hax at C7); 2.2-1.4 (m, 8 H, menthyl protons, CH (C12) ); 1.44 (s, 9 H, CH$_3$ t-butyl); 0.93 (d, 3H, $^3$J =6.63 Hz, CH$_3$ (C11)); 0.92 (d, 3 H, $^3$J =6.88 Hz, CH$_3$ (C13/14)); 0.75 (d, 3 H, $^3$J =6.78 Hz, CH$_3$ (C13/14))

δ$R^2$=C$_6$H$_5$ yield: 82% (oil)
Dibenzoyl peroxide was used as the free-radical initiator and benzene was used as the solvent. For working up, 5 ml 2 N HCl was added. Mobile phase: methylene chloride/methanol 99/1.
$^1$H-NMR (400 MHZ, CDCl$_3$): δ=8.77 (quin; 2 H, CH (C17/17'); 7.50 (sept, 3 H, CH (C18/18'/18") C19); 3.01 (s, 3 H, N—CH$_3$); 2.76 (m, 1 H, H$_{ax}$ at C7); 2.4-1.4 (m, 8 H, menthyl protons, CH (C12)); 0.97 (d, 3H, $^3$J 6.49 Hz, CH$_3$ (C11)); 0.95 (d, 3 H, $^3$J 6.82 Hz, CH$_3$ (13/14)); 0.70 (d, 3 H, $^3$J =6.87 Hz, CH$_3$ (13/14))

ω) $R^2$=adamantyl yield: 52% (oil) Bis-(trifluoroacetoxy)-iodo-benzene was used as the free-radical initiator. Mobile phase: methylene chloride/methanol =99:1
$^1$H-NMR (400 MHZ, CDCl$_3$): δ=2.84 (S, 3 H, N-CH$_3$); 2.63 (m, 1 H, H$_{ax}$ at C7); 2.29 (d, 3 H, CH (C18/18'18")); 2.2–1.3 (m, 8 H, menthyl protons, CH (C12)), 0.92 (d, 3H, $^3$J=6.50 Hz, CH$_3$ (C11)); 0.91 (d, 3 H, $^3$J =7.15 Hz, CH$_3$ (C13/14)); 0.76 (d, 3 H, $^3$J =6.88 Hz, CH$_3$ (C13/14))

TABLE V

Synthesis of compounds of the type VII a) starting from (−)-menthol

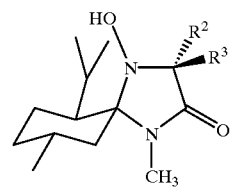

| $R^2$ | $R^3$ | Yield in % | M.p. in ° C. |
| --- | --- | --- | --- |
| CH$_3$ | CH$_2$CH=CH$_2$ | 54 | 151.2 |
| CH$_3$ | CH=CH$_2$ | 84 | 148.5 |
| CH$_2$CH$_3$ | CH$_3$ | 85 | 148.5 | b) starting from (+)-menthol

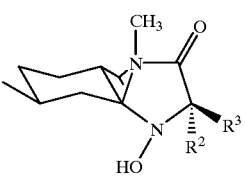

| $R^2$ | $R^3$ | Yield in % | M.p. in ° C. |
| --- | --- | --- | --- |
| CH$_3$ | C$_6$H$_5$ | 9 | 182.1 |
| CH$_3$ | p-Br—C$_6$H$_4$ | 13 | 153.3 |
| (CH$_3$)$_2$CH$_2$CH$_2$ | CH$_3$ | 69 | 201.4 |
| CH$_2$CH$_3$ | CH$_3$ | 56 | 142.1 |

TABLE VI

Synthesis of compounds of the type VIII (starting from (+)-menthol)

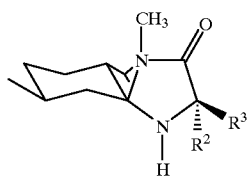

| R² | R³ | Yield in % | M.p. in °C. |
|---|---|---|---|
| CH₃ | C₆H₅ | 74 | — |
| (CH₃)₂CH₂CH₂ | CH₃ | 91 | 122.0 |
| CH₂CH₃ | CH₃ | 30 | 111.2 |

TABLE VII

Synthesis of compounds of the type X from IX via XI (starting from (−)-menthol

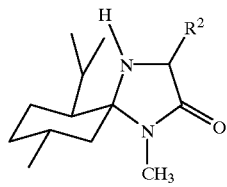

| R² | Yield in % | Optical rotation $[\alpha]_D^{20}$, CHCl₃ |
|---|---|---|
| CH₃ | 96 | — |
| CH₂CH₃ | 85 | −2.3 |

TABLE VIII

Synthesis of compounds of the type V with the aid of amino acid esters and (+)-menthone (The reactions are carried out analogously to the reactions to give compound type II)

| Amino acid | Solvent | Yield |
|---|---|---|
| L-Alanine | EtOH | 71% |
| L-Methionine | EtOH | 71% |
| L-Methylcysteine | EtOH | 75% |

The reaction of (−)-menthone with L-alanine in n-butanol gives a yield of 70% of compound type V.

TABLE 9

Hydrolysis to give the amino acids

| Amino acid | Yield in % | ee[a] in % |
|---|---|---|
| *Route A* | | |
| L-Alanine | 75 | >99.9 |
| L-Aminobutyric acid | 58 | >99 |
| L-Valine | 36 | >99 |
| L-Phenylalanine | 70 | >99 |
| L-Vinylglycine | 29 | 20 |
| L-tert-LeucinexHCLxXH₂O [sic] | −90 | >99 |

[a]The enantiomer purity was determined via HPLC after derivatization.

TABLE 9-continued

Hydrolysis to give the amino acids

| Amino acid | Yield in % | ee in % |
|---|---|---|
| *Route B* | | |
| D-Alanine | 73 | 99.8 |
| D-Aminobutyric acid | 91 | 99.3 |

12. Preparation of cis-4-hydroxyproline derivatives by cycloaddition using the example of cis-4-hydroxyproline 1) according to equation 1 a) Build-up of the isoxazolidine XVI with acrolein dimethyl acetals 500 mg (2.10 mmol) (5S,6S,9R)-6-isopropyl-4,9-dimethyl-1,4-diazaspiro[4.5]dec-1-en-3-one 1-oxide and 856 mg (8.40 mmol) acrolein dimethyl acetal are dissolved in toluene and the solution is boiled under reflux under an argon atmosphere for 18 h. The course of the reaction is monitored by means of thin layer chromatography and, optionally, the reaction time is extended until no further educt is present, since the chromatographic separation of educt and product presents problems. Unreacted acrolein methyl acetal is removed, together with the solvent, on a rotary evaporator and subsequently on a high vacuum apparatus. The pale yellow oily high-viscosity crude product, which foams severely in vacuo, can be further used directly for further reactions. For analytical purposes, it is purified by column chromatography (silica gel SG 60, CH₂Cl₂/MeOH 97/3). 607.7 mg (1.78 mmol, 85%) of the cycloadduct are obtained.

¹H-NMR (400 MHZ, CDCl₃):δ=4.29 (d, 1 H, ³J =6.01 Hz, CH (C18)); 3.94 (d, 1 H, ³J =8.96 Hz, CH (C2)); 3.86 (m, 1 H, CH (C17)); 3.44 (s, 1 H, OCH₃ (C19)); 3.41 (s, 1 H, OCH₃ (C19')); 2.74 (s, 3 H, N-CH₃); 2.67 (oct., 1 H, CH (C16)); 2.39 (sext., 1 H, CH (C16)); 2.1–1.1 (m, 8 H, menthyl protons, CH (C12)); 0.97 (d, 3 H, ³J =6.63 Hz, CH₃ (C11)); 0.88 (d, 3 H, ³J =6.93 Hz, CH₃ (C13/14)); 0.86 (d, 3 H, ³J =6.75 Hz, CH₃ (C13/14))

If acrolein diethyl acetal or 2-vinyl-1,3-dioxolane is used as the 1,3-dipolarophile, isoxazolidine derivatives analogous to XVI are isolated in a yield of 87% and 81% respectively.

b) Ring opening to give the compound of the type XVII

The hydrogenation catalyst (100 mg palladium on active charcoal) is initially introduced into a three-necked flask, the flask is flushed thoroughly with argon and the solvent is added. The catalyst is prehydrogenated and (400 mg (1.17 mmol)) of the cycloadduct, dissolved in 25 ml abs. methanol, are added dropwise via a septum. acuum is applied and the apparatus flushed with hydrogen several times. The hydrogen required for the reaction is fed in via the gas balloon technique. The mixture is stirred intensively for approx. 1 week, the hydrogen reservoir is replaced every 24 h and, after 3 days, the same amount of fresh catalyst is added once again via a Schlenk tube.

The catalyst is filtered off with suction over kieselguhr and the filtrate is freed from the solvent on a rotary evaporator and on a high vacuum apparatus. The crude product is purified by column chromatography (silica gel SG60, mobile phase: CH₂Cl₂/MeOH 97/3) to remove residual amounts of unreacted cycloadduct. The yield of the colourless viscous oil is 293 mg (0.86 mmol, 73%).

¹H-NMR (400 MHZ, CDCl₃); δ=4.70 (s, 1 H. NH-amine); 4.26 (d, 1 H, ³J =5.11 Hz, CH (C18)); 3.89 (oct. 1 H, CH (C17)); 3.76 (t, 1 H, ³J =6.17, CH (C2)); 3.48 (s, 6 H OCH₃ (Cl9/19')); 2.79 (s, 3 H, N-CH₃); 2.2–1.5 (m, 11

H. 8 menthyl protons, CH (C12)), $CH_2$ (C16)); 0.94 (d, 3 H, J =6.46 Hz, $CH_3$ (C11)); 0.91 (d, 6 H, $^3J$ =6.86 Hz, $CH_3$ (C13/14))

The correspondingly ring-opened products starting from acrolein diethyl acetal and 2-vinyl-1,3-dioxolane as the dienophile were isolated in a yield of 60% and 54% respectively.

c) Synthesis of (2S,5S,7S)-7-hydroxy-3-methyl-4-oxo-1, 3-diaza-bicyclo[3.3.0]-octane-2-[(2S,5R)-2-isopropyl-5-methyl]-spirocyclohexane (compound XVIII)

1.4 g (4.02 mmol) of the amino alcohol type XVII are suspended in 75 ml 1 N hydrochloric acid and the suspension is stirred for 2.5 h. During this period, the proline building block slowly dissolves and the clouding of the mixture disappears. The solvent is stripped off at room temperature on a high vacuum apparatus, the residue is taken up in 50 ml pH 4.62 buffer (acetic acid/acetate buffer, Riedel de Haen) and a total of 1.26 mg (20.1 mmol) sodium cyanoborohydride are added in portions. The mixture is stirred at RT for 5 days in total, and after 2 days another 0.63 g (10 mmol) $NaBH_3CN$ are subsequently metered in again. For working up, the reaction solution is carefully acidified with dil. HCl solution and extracted five times with 30 ml methylene chloride each time. The org. phase is dried over $MgSO_4$, the solvent is removed on a rotary evaporator and the product is dried under HV. 879 mg (3.13 mmol, 78%) of a colourless partly crystalline substance which corresponds to the desired product are isolated. Complete purification of the crude product is achieved by column chromatography (silica SG60, mobile phase: cyclohexane/isopropanol 8/2).

$R_f$ (product): 0.10 ($CH_2Cl_2$/MeOH 97/3)

$^1$H-NMR (400 MHZ, $CDCl_3$): δ=4.33 (t, 1 H, $^3J$ =4.80 Hz, CH (C17)); 3.72 (q, 1 H, $^3J$ =4.53 Hz, $^3J$ =8.98 Hz, CH (C2)); 3.16 (q, 1 H. $^3J$ =10.50 HZ, J =4.30 Hz, fH (C18)); 3.08 (q, 1 H, $^3J$ =10.46 Hz, $^3J$ =4.83 Hz, CH (C18)); 2.74 (s, 3 H, N-$CH_3$); 2.28-1.27 (m, 11 H, mentyl protons, CH (C12)), $CH_2$ (C16)); 0.96 (d, 3 H, $^3J$ =6.21 Hz, $CH_3$ C11)); 0.89 (d, 3 H, $^3J$ =6.69 Hz, $CH_3$ (C13/14)); 0.84 (d, 3 H, $^3J$ =6.80 Hz, $CH_3$ (C13/14))

Further reactions as described in J. Chem. Soc. Chem. Commune (11) 1291 (1994) lead to L-cis-4-hydroxyproline.

2) according to equation 2

Synthesis of (2S,5S,7S)-7-hydroxymethyl-3-methyl-4-oxo-8-oxs-1,3-diazabiocyclo [3.3.0]octane-2- [(2S, 5R)-2-isopropyl-5-methyl]spirocyclohexane (XIX)

((5S,6S,9R)-6-Isopropyl-4,9-dimethyl-1,4-diazaspiro [4.5]dec-1-ene-3-one 1-oxide (15.78 mmol, 4 g) and allyl alcohol (50.22 mmol, 2.92 g) are heated under reflux in 30 ml abs. toluene under argon for 5 h. After the solvent has been stripped off on a rotary evaporator and then under a high vacuum, the crude product is recrystallized from ethyl acetate. XIX (10.66 mmol, 3.16 g) is obtained as colourless crystals in a yield of 64%.

M.p.: 133.5° C. $[α]_D^{21}$=+69.8 (c =1.0, chloroform) $R_f$ value: 0.22 (methylene chloride/methanol =96.5:3.5)

Synthesis of (3S,5R,6S,9R)-3-[(2S)-2,3-dihydroxypropyll-6-isopropyl-1,9-dimethyl-2-oxo-1,4-diazaspiro[4. 5]decane (type V)

Compound type XIX (4.35 mmol, 1.29 g) in 40 ml abs. methanol is reacted in the presence of 0.4 g Pd/C (10%) under a hydrogen atmosphere at room temperature. After 8 h, the reaction solution is filtered over Celite, the catalyst is washed with methanol and the solvent is removed on a rotary evaporator. Drying under a high vacuum gives 1.29 g (99%) of colourless oil.

$[α]_D^{21}$=+14.2 (c =1.0, chloroform)

Synthesis of (3S,5S)-3-amino-5-hydroxymethyldihydro-2-furanone (XX)

3.62 mmol (1.08 g) (3S,5R,6S,9R)-3-[(2S)-2,3-dihydroxypropyl]-6-isopropyl-1,9-dimethyl-2-oxo-1,4-diazaspiro[4.5]decane are heated under reflux in 20 ml 5% HCl for 2 h. After extraction with 2×30 ml diethyl ether, the aqueous phase is evacuated. The crude product is purified by recrystallization from ethanol and water and gives colourless crystals in a yield of 74%.

M.p.: 230.0° C. (decomposition)

$[α]_D^{21}$=+27.1 (c =1.0, chloroform)

Synthesis of (2S,4S)-4,5-dihydroxynorvaline (XXI)

(3S,5S)-3-Amino-5-hydroxymethyldihydro-2-furanone XX (4.8 mmol, 0.80 g) is heated under reflux in 40 ml 6 N hydrochloric acid for 8 h. The reaction solution is evacuated and the residue is introduced on to a strongly acid ion exchanger column, which is then washed neutral with water. Thereafter, the amino acid XXI is eluted with 1.5 N ammonia solution. After the eluting agent has been stripped off, the crude product is recrystallized from water and ethanol. 365 mg (51%) of the colourless target compound of melting point 154° C. are obtained. 21

$[α]_D^{21}$=−23.9 (c =1.0, water) Further reactions analogously to J. Am. Chem. Soc. 1986, 108, 6041 lead to L-cis-4-hydroxyproline 13. Synthesis of N-hydroxy-amino acids and derivatives (general working instructions)

The synthesis is carried out via the chain tautomers of the compounds of the general formula VI 1) General preparation of the chain tautomer XIV (ring-opening reaction)

1.86 mmol of the compound type IV are dissolved in 25 ml absolute $THF_{abs}$ and the solution is cooled to −78° C. under argon. 1.1 equivalents of a 3 M methyl-Grignard solution are slowly added dropwise, while stirring thoroughly. The suspension formed is warmed to 20° C. and subsequently stirred (monitoring by TLC). 50 ml of a half-saturated $NH_4Cl$ solution are then added to the mixture. After the organic phase has been separated off, extraction is carried out twice more with diethyl ether and (he combined organic phases are dried over sodium sulphate. The E/Z isomers are obtained in a diastereomerically pure form by column chromatography.

a) Synthesis of (1S,2'S,5'R)-1-(N-methyl-1-carbamoyl)-propyl-(2'-isopropyl-5'-methyl)-cyclohexylidene-amine N-oxide (type XIV)

In accordance with the general working instructions, 500 mg (0.59 mmol) of the compound type IV where $R^1$=$CH_3$ and $R^2$=$CH_2CH_3$ are dissolved in 25 ml THFB, and reacted with 0.68 ml of a 3 M methylmagnesium bromide solution. After column chromatography in $CH_2Cl_2$/MeOH/$Et_3$N (96/3/1), the E/Z isomers are present as a colourless solid.

Yield: 81%

$R_f$: 0.2/0.27 ($CH_2Cl_2$/MeOH =95/5)

$^1$H-NMR (400 MHz, $CDCl_3$): δ=8.26 (s, broad, 1 H, CON$HCH_3$); 4.76 (dd, 1 H, $^3$JA =5.7 Hz, $^3$JB =8.6 Hz, CH-3); 3.51 (dm, 1 H, $^3$J =13.92 Hz, CHe-10); 2.76 (d, 3 H. $^3$J =4.9 Hz, CON$HCH_3$); 0.98 (t, 3 H , $^3$J =7.4 Hz, $CH_3$–17); 0.95 (d, 2 H, $^3$J=7.1 Hz, $CH_3$H1/13/14); 0.92 (d, 3 H, J=7.1 Hz, $CH_3$–3 11/13/14); 0.82 (d, 3 H, J =6.7 Hz, $CH_{3-11/13/14}$).

b) Synthesis of (lS,2'S,5'R)-1-(N-methyl-1-carbamoyl)-2, 2-dimethyl-propyl-(2'-isopropyl-5'-methyl)-cyclohexylidene-amine N-oxide (type XIV)

In accordance with the general working instructions, 220 mg (0.74 mmol) of the compound type IV where $R^1$=$CH_3$ and R²=C(CH₃)₃ are dissolved in 15 ml$_{THFabs}$ and reacted with 0.27 ml of a 3 M methylmagnesium bromide solution. After column chromatography in CH₂Cl₂/MeOH/Et₃N (96/3/1), the E/Z isomers are present as a colourless oil.

Yield: 62%

R$_f$: 0.48 (CH₂Cl₂/MeOH=95/5), UV

¹H-NMR (400 MHZ, CDCl₃, see fig. III-35, p. 57 [sic]):

E/Z isomers: δ=8.8/8.5 (s, broad, 1 H, CONHCH₃); 4.58/4.54 (s, 1 H. CH-3); 3.47 (dm, CH$_e$-10); 2.74/2.71 (d, 3 H, CONHCH₃, ³J =4.9 Hz); 2.46-0.79 menthyl and tert.butyl protons: 26 H, in these: 1.16/1.15 (s, 9 H, CH$_{3-17/18/19}$); 0.97 (d, 3 H, CH₃-11/13/14, ³J =6.5 Hz); 0.89 (d, 3 H, ³J =7.1 Hz, CH₃-11/13/14); 0.83 (d, 3 H, ³J =6.8 Hz, CH$_{3-11/13/14}$); 0.80 (d, 3 H, ³J =6.7 Hz, CH$_{3-11/13/14}$).

Further derivatives can be prepared by an analogous route:

c) (1S,2'S,5'R)-1-(N-Methyl-1-carbamoyl)-ethyl-(2'-isopropyl-5'-methyl)-cyclohexylidene-amine N-oxide Yield: 73%; E/Z ratio: 6/1 d) (1S,2'S,5'R)-1-(N-Methyl-1-carbamoyl)-2-methyl-propyl-(2'-isopropyl-5'-methyl)cyclohexylidene-amine N-oxide Yield: 64%; E/Z ratio: 3/1 .

Note: The nomenclature for the chain tautomer XIV is in accordance with Houben-Weyl "Methoden der Organischen Chemie [Methods of Organic Chemistry]", vol. E14b, part 2.

2) Hydrolysis to give the N-hydroxy-amino acids and derivatives a) N-Hydroxy-1-alanine methylamide hydrochloride 254 mg (1 mmol) (E)-(1S,2'S,5'R)-1-(N-methyl-1-carbamoyl)-ethyl-(2'-isopropyl-5'-methyl)-cyclohexylidene-amine N-oxide are dissolved in 4 ml 0.5 N HCl and the solution is left to stand for 2 h, During evaporation under a water pump vacuum, the menthone which has been liberated is also driven off. 170 mg of a yellowish viscous mass, which already proved to be very pure product by NMR spectroscopy, are obtained. The free base is obtained after ion exchange chromatography (DOWEX 50×W 8). After the ammoniacal solution has been evaporated on a rotary evaporator, an oil is present, from which the product is obtained as a white solid (110 mg) after addition of toluene and renewed evaporation on a rotary evaporator.

Yield: 93%

M.p.: 118.9 ° C.

Optical rotation: [α]$_D^{20}$=−2.5° C. (c =1.2, CHCl₃).

b) N-Hydroxy-1-valine N-methylamide hydrochloride 100 mg (0.35 mmol) (E)-(1S,2'S,5'R)-1-(N-methyl-1-carbamoyl)-2-methyl-propyl-(2'isopropyl-5'-methyl)-cyclohexylidene-amine N-oxide is taken up in 2 ml 1 N HCl and the mixture is left to stand at room temperature overnight. After evaporation in vacuo, the menthone which has been split off also being driven off, the vitreous solid is taken up in a little water again and the product is lyophilized. 63 mg of product are obtained as a white solid.

Yield: 97% c) N-Hydroxy-1-aminobutyric acid amide was obtained in a yield of 94% by an analogous reaction procedure.

What is claimed is:

1. A process for the preparation of optically active amino acid related compounds of the general formula Ia and acid addition salts thereof

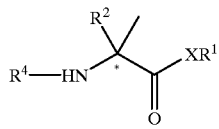

wherein

*=centre of asymmetry

X=O or NH

R¹=H, (C₁–C₆) alkyl, benzyl or (C₁–C₄) alkoxycarbonylmethyl and

R², denotes

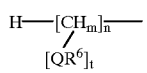

wherein m is 0,1, or 2 and n and t are 0–6 Q is H, N, P, O, S or Si,

R is H. (C₁–C₃) alkyl (C₂–C₆) alkenyl, (C₁–C₆) haloalkyl, halogen, aryl, said aryl being substituted by H, (C₁–C₃) alkyl, hydroxyl, halogen or (C₁–C₃) alkoxy, aryl, said aryl being substituted by H, (C₁–C₃) alkyl, hydroxyl, halogen or (C₁–C₃) alkoxy and heteroaralkyl, and R⁴=H, comprising the sequential steps of a) reacting a compound of formula II

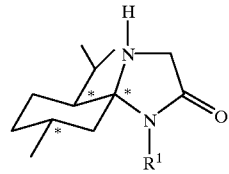

with an oxidizing agent to yield a compound of formula III

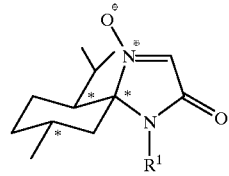

b) reacting the compounds of formula III with a nucleophile of formula R²Z where Z is a suitable leaving group to give compounds of formula IV

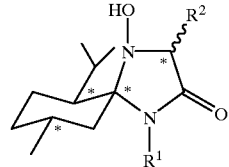

c) reacting the compounds of formula IV with a reducing agent to give the compounds of formula V

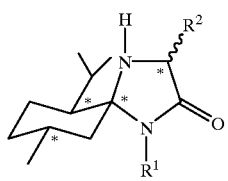
V and then
- d) hydrolyzing the compounds of formula V to give the L-α-amino acids or L-α-amino acid derivatives or D-α-amino acids or D-α-amino acid derivatives of the general formula I or of an acid addition salt thereof, or in that process steps a) and b) are carried out and then
- e) the compound of the general formula IV is oxidized to give compounds of the general formula VI

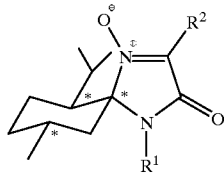
VI wherein *, $R^1$ and $R^2$ have the meaning already given, and VI is converted by reaction with a nucleophile into compounds of the general formula VII

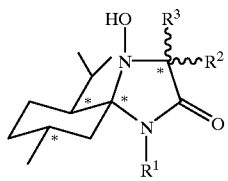
VII wherein *, $R^1$, $R^2$ and $R^3$ have the meaning already given, and
- f) compounds of the general formula VII are reduced to give compounds of the general formula VIII

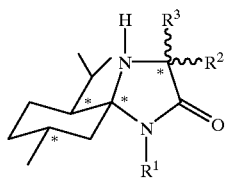
VIII wherein *, $R^1$, $R^2$ and $R^3$ have the abovementioned meaning, and then
- g) these are hydrolysed to give the α,α-dialkylamino acids or α,α-dialkylamino acid derivatives of the general formula I or of an acid addition salt thereof].

2. The process according to claim 1, wherein $R^1$ $(C_1-C_4)$ alkyl or benzyl, and H provided that than X=O.

3. A process for the preparation of optically active amino acid related compounds of formula Ia and acid addition salts thereof

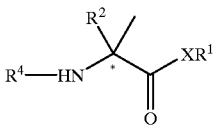
Ia wherein
* = centre of asymmetry
X = O or NH
$R^1$ = H, $(C_1-C_6)$ alkyl, benzyl or $(C_1-C_4)$ alkoxycarbonylmethyl and
$R^2$, denotes

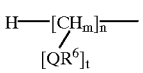

wherein m is 0.1. or 2 and n and t are 0-6
Q is N, P, O, S or Si,
$R^6$ is H, $(C_1-C_3)$ alkyl $(C_2-C_6)$ alkenyl, $(C_1-C_6)$ haloalkyl, halogen, aryl, said aryl being substituted by H, $(C_1-C_3)$ alkyl, hydroxyl, halogen or $(C_1-C_3)$ alkoxy, aralkyl, said aralkyl being substituted by K $(C_1-C_3)$ alkyl, hydroxyl, halogen or $(C_1-C_3)$ alkoxy and heteroaralkyl, and
$R^4$=H, comprising the sequential steps of
a) dehydrating the compounds of formula

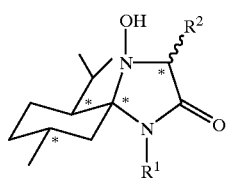
IV prepared in accordance with claim 1 from the nitrone III

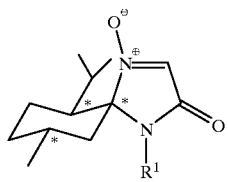
III as defined in claim 1 to give compounds of formula XI

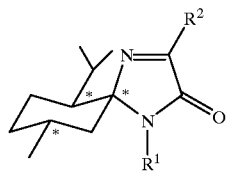
XI and
b) reacting the compounds of formula Xl with a reducing agent whereby they are inverted to yield compounds of formula XII and compounds of XIII

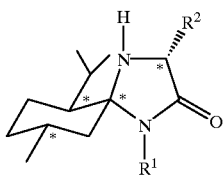
XII

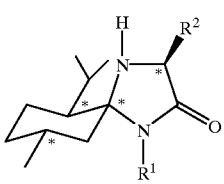
XIII c) hydrolyzing the compounds of formulae XII and XIII.

4. A process for the preparation of optically active N-hydroxy-amino acids of formula Ia as defined in claim 1,

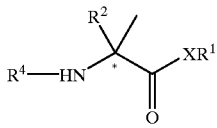
Ia comprising the steDs of reacting compounds of formula IV as defined in claim 1
  a) with an organometallic reagent to give compounds of formula XIV

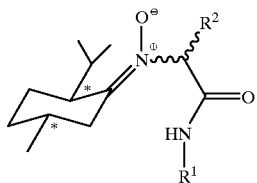
XIV and
  b) further reacting comDonds of formula XIV with an acid.

5. A process for the synthesis of compounds of formula II as defined in claim 1 which comprises carrying out said synthesis in the presence of a water-binding agent.

6. The process according to claim 1 comprising carrying out the reactions of the compounds of formula III to give compounds of formula IV in diethyl ether, tetrahydrofuran or toluene.

7. The process according to claim 1 comprising carrying out the reactions of the compounds of formula III to give the compounds of formula IV are carried out at temperatures from −20° C. to −80° C.

8. The process according to claim 1 where in the reducing agent for reducing the compounds of formula IV to give the compounds of formula V is hydrogen in the presence of Pd or Pt on active charcoal in hydrochloric acid solution or of Raney nickel in alcohol.

9. A process according for the formation of a compound of formula VI as defined in claim 1 directly from compounds of formula III

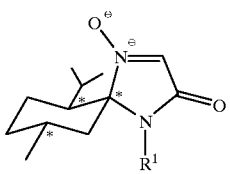
III comprising adding a carboxylic acid of the formula $R^2CO_2H$, wherein $R^2$ is defined in claim 1, in the presence of a free-radical initiator.

10. The process according to claim 9, wherein the free-radical initiator is dibenzoyl peroxide, azobisisobutyronitrile, $K_2S_2O_8/AgNO_3$ or $PhI(CF_3CO_2)_2$.

11. The process according to claim 9, wherein the organic solvent is an aromatic hydro-carbon.

12. A process for the preparation of compounds of formula V as defined in claim 1

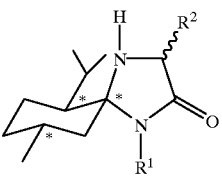
V which comprises reacting an amino acid derivative of the formula XXII a

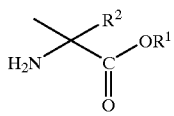
XXIIa wherein $R^1$, and $R^2$ have the meaning given in claim 1, or an acid addition salt thereof, with D- or L-menthone in the presence of a primary amine in the presence of an organic solvent.

13. A process according to claim 14, wherein the organic solvent is an alcohol.

14. A process for the preparation of cis-4-hydroxy-proline precursors, comprising
  a) reacting compounds of formula III as defined in claim 1

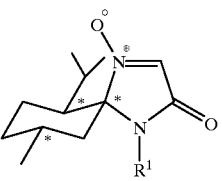
III wherein
  $R^1$=H, $(C_1-C_6)$ alkyl, benzyl or
  $(C_1-C_4)$ alkoxycarbonylmethyl, with an acrolein acetal in a 1,3-dipolar cycloaddition to give compounds of formula XVI

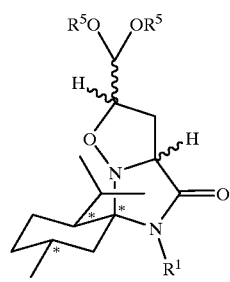

XVI wherein $R^5 = CH_3$, $CH_2CH_3$, or when $CH_2CH_2$ can be joined to one another to give a five-membered heterocyclic ring, b) reacting the compounds of formula XVI with a reducing agent to give compounds of formula XVII

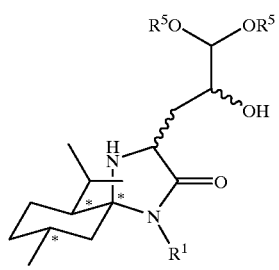

XVII and treating sequentially with
c) with aqueous acid and then
d) with a reducing agent to give compounds of formula XVIII.

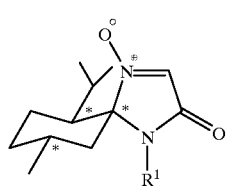

XVIII

15. A process process for the preparation of cis-4-hydroxyproline precursors, comprising
a) reacting compounds of formula III as defined in claim 1

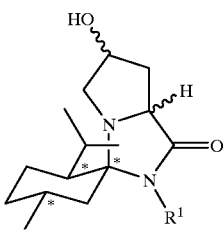

III wherein
$R^1 = H$, $(C_1-C_6)$ alkyl, benzyl or $(C_1-C_4)$ alkoxycarbonylmethyl, with allyl alcohol, to give compounds of formula XIX

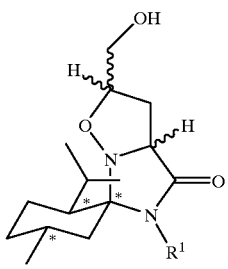

XIX b) reacting the compounds of formula XIX with a reducing agent to give compounds of formula V as defined in claim 1 having the specific structure

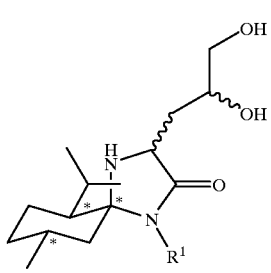

V and then subjecting them to acid hydrolysis to yield compounds of formulae XX and XXI

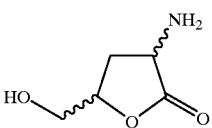

XX

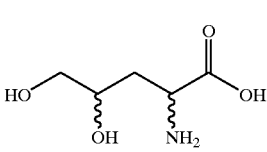

XXI

16. A compound of formula XVI as defined in claim 14

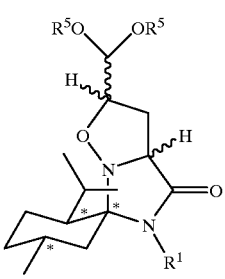

XVI wherein
* denotes a centre of asymmetry and
$R^1 = H$, $(C_1-C_8)$ alkyl, benzyl or $(C_1-C_4)$ alkoxycarbonylmethyl and wherein $R^5 = CH_3$, $CH_2CH_3$, or when $CH_2CH_2$ can be joined to one another to give a five-membered heterocyclic ring.

17. A compound of formula XVIII as defined in claim 14

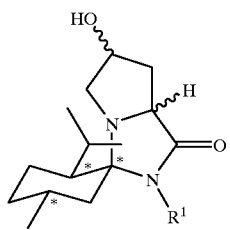

XVIII wherein
* denotes a centre of asymmetry and
$R^1$=H, ($C_1$–$C_6$) alkyl, benzyl or
$C_1$–$C_4$ alkoxycarbonylmethyl.

18. A compound of formula XIX a defined in claim 15

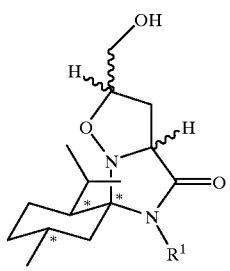

XIX wherein
* denotes a centre of asymmetry and
$R^1$ =H, ($C_1$–$C_6$) alkyl, benzyl or
$C_1$–$C_4$ alkoxycarbonylmethyl.

19. A process for the preparation of optically active amino acid related compounds of the general formula I and acid addition salts thereof

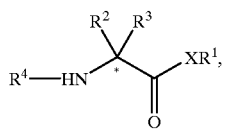

I wherein
*=centre of asymmetry
X=O or NH
$R^1$=H, ($C_1$–$C_6$) alkyl, benzyl or
($C_1$–$C_4$) alkoxycarbonylmethyl and
$R^2$,$R^3$, independently of one another, denote

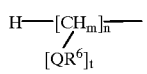

wherein m is 0,1, or 2 and n and t are 0–6 Q is N, P, O, S or Si,
$R^6$ is H, ($C_1$–$C_3$) alkyl, ($C_2$–$C_6$) alkenyl, ($C_1$–$C_6$) haloalkyl, halogen, aryl. said arvl being substituted by H, ($C_1$–$C_3$) alkyl, hydroxyl, halogen or ($C_1$-$C_3$) alkoxy, aralkyl said aralkyl being substituted by H, ($C_1$–$C_3$) alkyl, hydroxyl, halogen or ($C_1$–$C_3$) alkoxy and heteroaralkyl, and $R^4$=H,
wherein if $R^2$=H, $R^3$+H, comprising the sequential steps of
a) reacting a compound of formula II

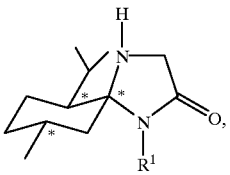

II with an oxidizing agent to yield a compound of formula III

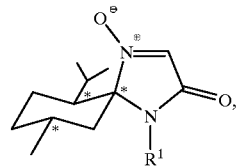

III b) reacting the compound of formula III with a nucleophile of formula $R^2$H to give compounds of formula IV

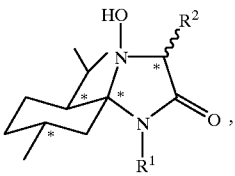

IV c) reacting the compound of formula IV with an oxidizing agent to yield compounds of formula VI

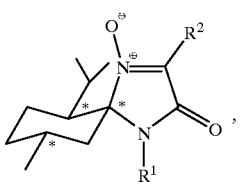

VI d) reacting the copounds of formula VI with a nucleophile of formula $R^2$Z wherein Z is a suitable leaving group to give compounds of formula VII

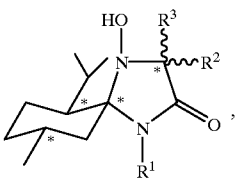

VII e) reacting the compounds of formula VIII with a reducing agent to yield compounds of the general formula VIII

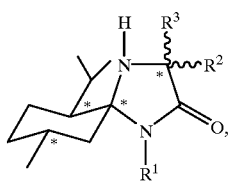

VIII and then d) hydrolyzing.

20. A process according to claim 19 wherein the reactions of the compounds of formula VI to give the compounds of formula VII are carried out at temperatures from +80° C, to −50° C.

21. A process according to claim 20, comprising performing the reaction in toluene.

22. Process according to claim 19, wherein $R^1=(C_1-C_4)$ alkyl or benzyl, and H provided and if $R^2$=H, $R^3$ H.

23. Process according for the preparation of compounds of formula VIII as defined in claim 19.

VIII

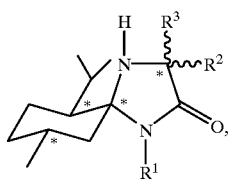

which comprises reacting an amino acid derivative of the formula XXII

XXII

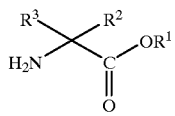

wherein $R^1$, $R^2$ and $R^3$ have the meaning given in claim 19, or an acid addition salt thereof, with D- or L-menthone and an amine, in the presence of an amine and an organic solvent.

24. Process according to claim 23, wherein the organic solvent is an alcohol.

25. Process according to claim 24, wherein the alcohol is methanol, ethanol, isopropanol, n-butanol, tert.butanol or sec.butanol.

26. Process according to claim 13 wherein the alcohol is methanol, ethanol, isopropanol, n-butanol, tert.butanol or sec.butanol.

27. Process according to claim 12 wherein the reaction is carried out in the presence of methylamine, ethylamine, propylamine, benzylamine or isopropylamine.

28. Process according to claim 29 wherein the reaction is carried out in the presence of methylamine, ethylamine, propylamine, benzylamine or isopropylamine.

\* \* \* \* \*